(12) United States Patent
Ciancimino et al.

(10) Patent No.: US 11,401,269 B2
(45) Date of Patent: Aug. 2, 2022

(54) INTERMEDIATES AND PROCESSES FOR THE PREPARATION OF LINAGLIPTIN AND ITS SALTS

(71) Applicant: CAMBREX PROFARMACO MILANO S.R.L., Paullo (IT)

(72) Inventors: Cristina Ciancimino, Paullo (IT); Michele Tragni, Paullo (IT); Daniele Vigo, Paullo (IT); Oreste Piccolo, Sirtori (IT)

(73) Assignee: CAMBREX PROFARMACO MILANO S.R.L., Paullo (IT)

( * ) Notice: Subject to any disclaimer, the term of this patent is extended or adjusted under 35 U.S.C. 154(b) by 0 days.

(21) Appl. No.: 17/053,154

(22) PCT Filed: May 13, 2019

(86) PCT No.: PCT/EP2019/062229
§ 371 (c)(1),
(2) Date: Nov. 5, 2020

(87) PCT Pub. No.: WO2019/219620
PCT Pub. Date: Nov. 21, 2019

(65) Prior Publication Data
US 2021/0238178 A1 Aug. 5, 2021

(30) Foreign Application Priority Data
May 15, 2018 (IT) .................. 102018000005383

(51) Int. Cl.
*C07D 473/04* (2006.01)
(52) U.S. Cl.
CPC ................... *C07D 473/04* (2013.01)

(58) Field of Classification Search
CPC ..................... C07D 473/04; A61K 31/522
USPC ........................ 544/268; 514/263.1
See application file for complete search history.

(56) References Cited

U.S. PATENT DOCUMENTS

| | | | |
|---|---|---|---|
| 7,407,955 B2 | 8/2008 | Himmelsbach et al. |
| 7,820,815 B2 | 10/2010 | Pfrengle et al. |
| 8,865,729 B2 | 10/2014 | Sieger et al. |
| 8,883,805 B2 | 11/2014 | Pfrengle et al. |
| 9,056,112 B2 | 6/2015 | Haldar et al. |
| 9,353,114 B2 | 5/2016 | Singh et al. |
| 2009/0192314 A1 | 7/2009 | Pfrengle et al. |

FOREIGN PATENT DOCUMENTS

| | | |
|---|---|---|
| CN | 105541844 | 5/2016 |
| EP | 2 468 749 | 6/2012 |
| WO | 2016/207364 | 12/2016 |

OTHER PUBLICATIONS

International Search Report for PCT/EP2019/062229 dated Jul. 19, 2019, 5 pages.
Written Opinion of the ISA for PCT/EP2019/062229 dated Jul. 19, 2019, 5 pages.
Eckhardt et al., "8-(3-(R)-Aminopiperidin-1-yl)-7-but-2-ynyl-3-methyl-1-(4-methyl-quinazolin-2-ylmethyl)-3,7-dihydropurine-2,6-dione (BI 1356), a Highly Potent, Selective, Long-Acting, and Orally Bioavailable DPP-4 Inhibitor for the Treatment of Type 2 Diabetes":, Journal of Medicinal Chemistry, American Chemical Society, Dec. 1, 2007, vol. 50, No. 26, pp. 6450-6453.

*Primary Examiner* — Jeffrey H Murray
(74) *Attorney, Agent, or Firm* — Nixon & Vanderhye

(57) ABSTRACT

Disclosed are new intermediates for the synthesis of Linagliptin and of its salts and a process for its preparation involving said intermediates.

15 Claims, 12 Drawing Sheets

Figure 1 (continued)

Peak list –XRPD figure 1

| Name | Angle | d Value | Gross Intensity | Rel. Intensity |
|---|---|---|---|---|
| Peak #1 | 4.507 | 19.58811 | 9029 | 100.0% |
| Peak #2 | 9.392 | 9.40936 | 1865 | 18.7% |
| Peak #3 | 10.761 | 8.21480 | 1018 | 8.5% |
| Peak #4 | 11.768 | 7.51420 | 2587 | 26.2% |
| Peak #5 | 12.611 | 7.01355 | 1662 | 15.7% |
| Peak #6 | 12.914 | 6.84954 | 1553 | 14.5% |
| Peak #7 | 14.440 | 6.12927 | 948 | 7.4% |
| Peak #8 | 15.641 | 5.66105 | 3311 | 34.0% |
| Peak #9 | 16.245 | 5.45202 | 2638 | 26.3% |
| Peak #10 | 16.479 | 5.37496 | 2409 | 23.7% |
| Peak #11 | 18.870 | 4.69889 | 2373 | 22.4% |
| Peak #12 | 19.399 | 4.57193 | 1151 | 8.3% |
| Peak #13 | 19.766 | 4.48800 | 1426 | 11.4% |
| Peak #14 | 20.103 | 4.41345 | 1241 | 9.2% |
| Peak #15 | 20.888 | 4.24931 | 909 | 5.3% |
| Peak #16 | 21.435 | 4.14211 | 839 | 4.6% |
| Peak #17 | 21.870 | 4.06069 | 856 | 4.9% |
| Peak #18 | 23.150 | 3.83896 | 2379 | 22.0% |
| Peak #19 | 24.417 | 3.64255 | 1213 | 8.7% |
| Peak #20 | 25.302 | 3.51716 | 931 | 5.7% |

Figure 4 (continued)

Peak list –XRPD figure 4

| Name | Angle | d Value | Gross Intensity | Rel. Intensity |
|---|---|---|---|---|
| Peak #1 | 4.511 | 19.57240 | 8805 | 100.0% |
| Peak #2 | 9.386 | 9.41460 | 1467 | 14.7% |
| Peak #3 | 10.747 | 8.22530 | 797 | 6.4% |
| Peak #4 | 11.760 | 7.51945 | 1927 | 19.3% |
| Peak #5 | 12.613 | 7.01233 | 1532 | 14.6% |
| Peak #6 | 12.912 | 6.85060 | 1384 | 12.9% |
| Peak #7 | 14.435 | 6.13099 | 754 | 5.4% |
| Peak #8 | 15.646 | 5.65932 | 2831 | 29.3% |
| Peak #9 | 16.241 | 5.45336 | 2568 | 26.2% |
| Peak #10 | 16.482 | 5.37409 | 2193 | 21.8% |
| Peak #11 | 18.873 | 4.69824 | 2000 | 18.6% |
| Peak #12 | 19.410 | 4.56955 | 1093 | 7.8% |
| Peak #13 | 19.771 | 4.48676 | 1334 | 10.5% |
| Peak #14 | 20.104 | 4.41329 | 1204 | 8.8% |
| Peak #15 | 20.926 | 4.24183 | 846 | 4.5% |
| Peak #16 | 21.535 | 4.12308 | 927 | 5.4% |
| Peak #17 | 21.891 | 4.05691 | 813 | 4.2% |
| Peak #18 | 23.149 | 3.83913 | 2119 | 19.3% |
| Peak #19 | 24.418 | 3.64243 | 1109 | 7.5% |
| Peak #20 | 25.326 | 3.51386 | 790 | 4.1% |

Figure 7 (continued)

Peak List XRPD (Linagliptin - Mixture of polymorphs A/B):

| Pos. [°2θ] | Height [cts] | FWHM Left [°2θ] | d-spacing [Å] | Rel. Int. [%] |
|---:|---:|---:|---:|---:|
| 5.5670 | 46.61 | 0.2362 | 15.87521 | 0.93 |
| 7.1936 | 1166.64 | 0.0787 | 12.28890 | 23.18 |
| 7.6910 | 5034.00 | 0.1378 | 11.49509 | 100.00 |
| 7.8964 | 930.29 | 0.0787 | 11.19665 | 18.48 |
| 8.5503 | 555.38 | 0.1574 | 10.34168 | 11.03 |
| 9.4611 | 251.72 | 0.1968 | 9.34809 | 5.00 |
| 9.8549 | 301.37 | 0.1771 | 8.97539 | 5.99 |
| 10.4449 | 227.68 | 0.1968 | 8.46975 | 4.52 |
| 11.2013 | 563.72 | 0.0787 | 7.89939 | 11.20 |
| 11.7626 | 1262.09 | 0.1574 | 7.52373 | 25.07 |
| 12.4556 | 3400.36 | 0.2165 | 7.10662 | 67.55 |
| 12.6969 | 989.93 | 0.0590 | 6.97207 | 19.66 |
| 13.1173 | 482.55 | 0.2362 | 6.74959 | 9.59 |
| 13.9323 | 755.65 | 0.0787 | 6.35650 | 15.01 |
| 14.7661 | 372.10 | 0.1968 | 5.99940 | 7.39 |
| 15.3094 | 1234.92 | 0.1968 | 5.78772 | 24.53 |
| 15.6818 | 554.14 | 0.1968 | 5.65111 | 11.01 |
| 16.6518 | 483.97 | 0.1574 | 5.32402 | 9.61 |
| 17.6091 | 458.46 | 0.2362 | 5.03670 | 9.11 |
| 18.1946 | 341.66 | 0.1968 | 4.87591 | 6.79 |
| 18.9526 | 535.43 | 0.2165 | 4.68257 | 10.64 |
| 19.5664 | 743.90 | 0.1968 | 4.53704 | 14.78 |
| 19.8808 | 598.78 | 0.1181 | 4.46599 | 11.89 |
| 20.3259 | 534.38 | 0.1574 | 4.36919 | 10.62 |
| 21.4955 | 823.05 | 0.1968 | 4.13403 | 16.35 |
| 22.4349 | 961.14 | 0.1574 | 3.96302 | 19.09 |
| 23.1295 | 2343.94 | 0.0984 | 3.84554 | 46.56 |
| 23.5950 | 1664.27 | 0.0984 | 3.77072 | 33.06 |
| 24.9643 | 2161.37 | 0.1574 | 3.56691 | 42.94 |
| 25.1914 | 2706.06 | 0.1378 | 3.53527 | 53.76 |
| 25.8219 | 2907.31 | 0.2165 | 3.45037 | 57.75 |
| 26.5891 | 530.77 | 0.1968 | 3.35253 | 10.54 |
| 28.3315 | 838.08 | 0.3149 | 3.15019 | 16.65 |
| 28.8763 | 1184.22 | 0.1574 | 3.09197 | 23.52 |
| 30.2701 | 758.51 | 0.2362 | 2.95270 | 15.07 |
| 31.8195 | 155.68 | 0.7872 | 2.81237 | 3.09 |
| 33.9816 | 196.64 | 0.6298 | 2.63822 | 3.91 |
| 34.8932 | 161.83 | 0.3149 | 2.57136 | 3.21 |
| 37.5404 | 90.46 | 0.3936 | 2.39590 | 1.80 |
| 38.5714 | 60.97 | 0.4723 | 2.33420 | 1.21 |
| 39.6314 | 54.06 | 0.7872 | 2.27418 | 1.07 |
| 42.9242 | 80.62 | 0.7872 | 2.10705 | 1.60 |
| 46.9688 | 92.51 | 0.4723 | 1.93460 | 1.84 |
| 49.5080 | 89.41 | 0.6298 | 1.84116 | 1.78 |
| 51.6979 | 139.02 | 0.4723 | 1.76820 | 2.76 |
| 52.8271 | 84.66 | 0.4723 | 1.73304 | 1.68 |

Figure 8 (continued)

Peak List XRPD (Linagliptin - Polymorph A):

| Pos. [°2θ] | Height [cts] | FWHM Left [°2θ] | d-spacing [Å] | Rel. Int. [%] |
|---|---|---|---|---|
| 5.5843 | 39.99 | 0.2362 | 15.82622 | 0.91 |
| 7.2055 | 1207.97 | 0.1378 | 12.26864 | 27.45 |
| 7.6663 | 4400.19 | 0.1574 | 11.53219 | 100.00 |
| 8.5369 | 738.27 | 0.1378 | 10.35791 | 16.78 |
| 9.8496 | 443.79 | 0.1574 | 8.98028 | 10.09 |
| 10.4434 | 363.12 | 0.0787 | 8.47091 | 8.25 |
| 11.1559 | 838.58 | 0.1378 | 7.93143 | 19.06 |
| 11.7270 | 1269.62 | 0.2165 | 7.54645 | 28.85 |
| 12.4405 | 3297.45 | 0.1968 | 7.11522 | 74.94 |
| 13.1964 | 365.68 | 0.2362 | 6.70928 | 8.31 |
| 14.0878 | 437.62 | 0.1574 | 6.28672 | 9.95 |
| 14.3714 | 295.23 | 0.1181 | 6.16328 | 6.71 |
| 14.7487 | 532.65 | 0.1181 | 6.00646 | 12.11 |
| 15.3104 | 1096.34 | 0.1181 | 5.78732 | 24.92 |
| 15.7671 | 354.72 | 0.2362 | 5.62072 | 8.06 |
| 16.6760 | 416.44 | 0.2362 | 5.31636 | 9.46 |
| 17.0516 | 213.20 | 0.1181 | 5.20007 | 4.85 |
| 17.6105 | 424.98 | 0.1181 | 5.03630 | 9.66 |
| 18.1924 | 276.43 | 0.1574 | 4.87649 | 6.28 |
| 18.8529 | 569.66 | 0.0984 | 4.70710 | 12.95 |
| 19.8774 | 824.32 | 0.1574 | 4.46675 | 18.73 |
| 20.2993 | 612.37 | 0.1574 | 4.37486 | 13.92 |
| 21.5351 | 916.82 | 0.2755 | 4.12652 | 20.84 |
| 22.4415 | 1127.52 | 0.2362 | 3.96185 | 25.62 |
| 23.0930 | 2946.45 | 0.1968 | 3.85154 | 66.96 |
| 23.4474 | 1444.96 | 0.1574 | 3.79413 | 32.84 |
| 24.9619 | 2434.88 | 0.1574 | 3.56725 | 55.34 |
| 25.1794 | 2945.79 | 0.1181 | 3.53693 | 66.95 |
| 25.8021 | 2791.70 | 0.2165 | 3.45297 | 63.45 |
| 26.8385 | 393.64 | 0.4723 | 3.32193 | 8.95 |
| 27.4868 | 390.41 | 0.1574 | 3.24504 | 8.87 |
| 28.2920 | 599.30 | 0.1968 | 3.15449 | 13.62 |
| 28.9037 | 1185.11 | 0.2362 | 3.08911 | 26.93 |
| 30.2308 | 852.88 | 0.1181 | 2.95646 | 19.38 |
| 31.3319 | 71.75 | 0.4723 | 2.85502 | 1.63 |
| 34.8414 | 131.08 | 0.3149 | 2.57507 | 2.98 |
| 37.6167 | 78.57 | 0.4723 | 2.39121 | 1.79 |
| 41.6550 | 70.01 | 0.5510 | 2.16826 | 1.59 |
| 42.9260 | 81.67 | 0.7872 | 2.10696 | 1.86 |
| 46.9621 | 105.33 | 0.9446 | 1.93486 | 2.39 |
| 49.3719 | 144.91 | 0.3149 | 1.84592 | 3.29 |
| 51.7243 | 151.78 | 0.4723 | 1.76736 | 3.45 |
| 52.7558 | 96.93 | 0.4723 | 1.73521 | 2.20 |
| 55.7681 | 63.64 | 0.4723 | 1.64842 | 1.45 |

INTERMEDIATES AND PROCESSES FOR THE PREPARATION OF LINAGLIPTIN AND ITS SALTS

This application is the U.S. national phase of International Application No. PCT/EP2019/062229 filed May 13, 2019 which designated the U.S. and claims priority to IT Patent Application No. 102018000005383 filed May 15, 2018, the entire contents of each of which are hereby incorporated by reference.

TECHNICAL FIELD

The present invention relates to new intermediates for the synthesis of Linagliptin and its salts and a process for its preparation comprising said intermediates.

BACKGROUND ART (R)-8-(3-Aminopiperidin-1-yl)-7-(but-2-yn-1-yl)-3-methyl-1-((4-methylquinazolin-2-yl)methyl)-3,7-dihydro-1H-purine-2,6-dione, whose international nonproprietary name is Linagliptin (Formula I)

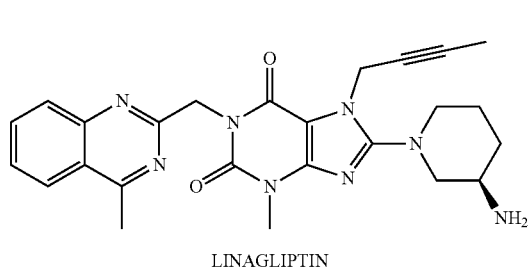

LINAGLIPTIN is a selective inhibitor of the enzyme DPP-4 (Dipeptidyl peptidase 4) which inactivates the incretins GLP-1 and GIP. Said incretins increase insulin biosynthesis and its secretion from pancreatic beta cells in the presence of normal and elevated blood glucose levels; in addition, GLP-1 also reduces glucagon secretion from pancreatic alpha cells, which leads to a reduction in hepatic glucose production. Linagliptin reversibly binds DPP-4, leading to a sustained increase and prolongation of active incretin levels and therefore increasing glucose-dependent secretion of insulin and decreasing glucagon secretion.

Linagliptin was developed by Boehringer Ingelheim for the treatment of type 2 diabetes mellitus and placed on the market with the names Tradjenta (in USA) and Trajenta.

Several methods for the preparation of Linagliptin are known in the art.

U.S. Pat. No. 7,407,955 and *J. Med. Chem.* 2007, 50, 6450-6453 disclose the synthesis of Linagliptin and its salts through a condensation reaction of 8-bromo-7-(but-2-yn-1-yl)-3-methyl-1-((4-methylquinazolin-2-yl)methyl)-3,7-dihydro-1H-purine-2,6-dione (II) with BOC-protected (R)-piperidin-3-amine (IIIa, PG=COOt-Bu), subsequent removal of the protective group (PG) in the presence of trifluoroacetic acid and optional subsequent salification with an organic or inorganic acid (Scheme 1; PG=COOt-Bu).

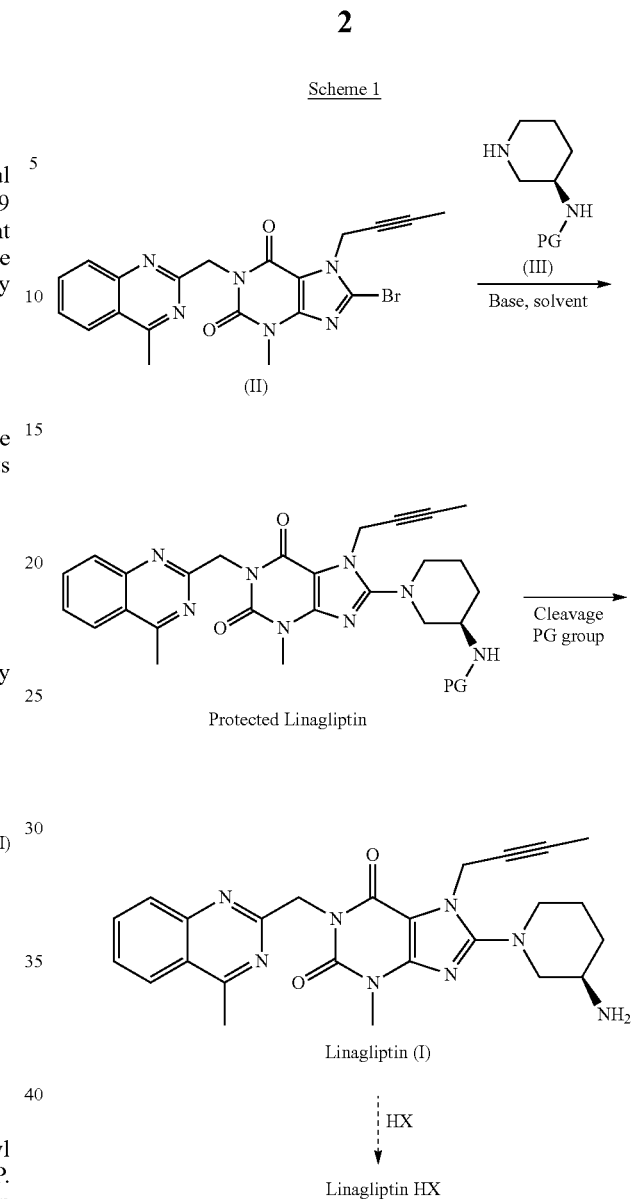

Scheme 1

Compound (1) is purified by silica gel column chromatography. This procedure is not suitable for commercial preparations of course.

The Applicant experimentally verified the above-mentioned deprotection procedure (see Ref. Example A). The process is characterised by extremely low yields (<50%) and good enough purity (<99.5%).

It is worth emphasizing that the intrinsic danger of TFA, the poor yield of the finished product obtained from said procedure and the high cost of the BOC-protected aminopiperidine, constitute a limit in the use of this process for industrial purposes.

U.S. Pat. No. 8,865,729 discloses pharmacologically acceptable salts of Linagliptin and in particular organic solvates, hydrated salts and mixtures of organic solvates and hydrates are described.

U.S. Pat. No. 7,820,815 describes a process similar to that shown in Scheme 1 but using the compound IIIb, wherein PG is a phthalimide group (Scheme 2).

Scheme 2

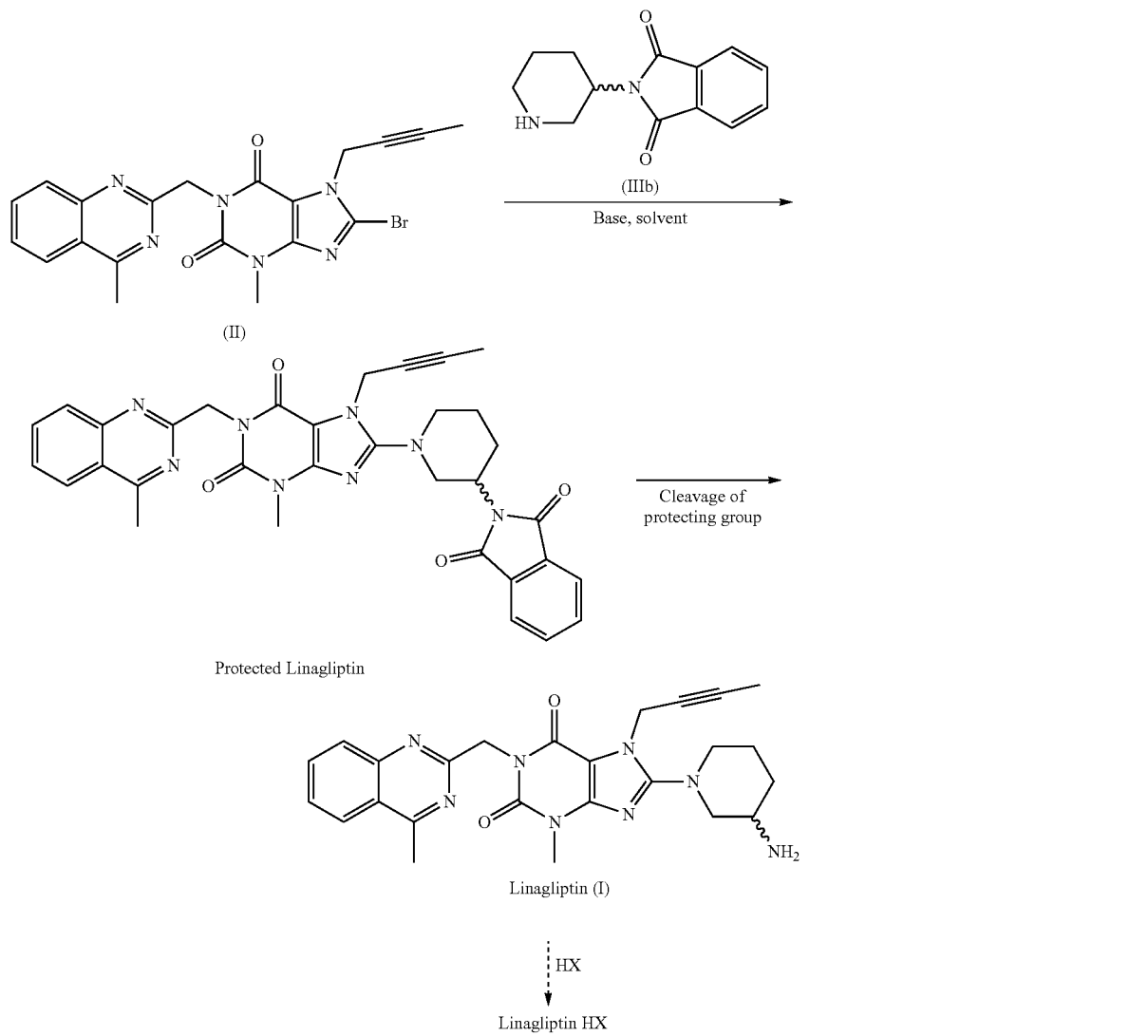

Linagliptin protected with the phthalimide group is specifically disclosed in U.S. Pat. No. 8,883,805: the deprotection reaction is carried out by treatment with ethanolamine in toluene or in tetrahydrofuran/water; subsequent phase separation and crystallization treatments are required to obtain a product with high yield. Purity is not indicated in the document.

The Applicant experimentally carried out the deprotection of the phthalimide intermediate according to the procedures reported in U.S. Pat. No. 8,883,805 (see Ref. Example B—Methods 1 and 2). Linagliptin obtained by the above mentioned process contains some amounts of phthalimide degradation products difficult to remove. Said by-products cause a decrease in overall yield (about 75-85%) and purity (about 95.5-97.5%) even after recrystallization procedure.

U.S. Pat. No. 9,353,114 discloses the preparation of Linagliptin through an intermediate characterized by a substituted phthalimide group. The compound (I) is obtained with high purity after the preparation of the Linagliptin salt with dibenzoyl-D-tartaric acid, crystallization and subsequent release of compound (I).

U.S. Pat. No. 9,056,112 refers to the reaction between the compound (II) and the unprotected compound (IIIc, where PG=H).

WO 2016/207364 discloses the reaction of (IIIc) with the chlorinated or iodinated analogue of the compound (II).

However, the use of (IIIc) produces the formation of the regioisomer (IV) of Linagliptin, as by-product (IV)

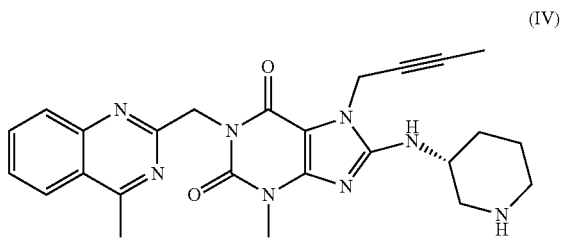 [SMILES: CC#CCn1c(N[C@@H]2CCCNC2)nc2c1c(=O)n(Cc1nc(C)c3ccccc3n1)c(=O)n2C]

which is difficult to remove by simple crystallization of (I). It is therefore necessary to transform the compound (I) into its salt, in particular into the corresponding (D)-tartrate, crystallize said salt and subsequently release compound (I) in basic conditions. This purification procedure, involving the formation of a Linagliptin salt, is effective for obtaining compound (I) with high purity, but also involves a worsening in terms of costs and environmental impact caused by the reaction waste disposal.

CN 105 541 844 refers to a process for obtaining a high purity HPLC product (I) without the salt formation by using the unprotected compound (Mc); however the used chromatographic conditions are not indicated and no mention is made about the content of regioisomer (IV). The Applicant has experimentally determined that using the procedure described in CN 105 541 844 the final content of regioisomer (IV) is about 0.2% which is not usually acceptable for an API.

The applicant has also carried out purity analysis of the active ingredient currently on the market (Tradjenta®), highlighting the presence of allene by-products in the impurities.

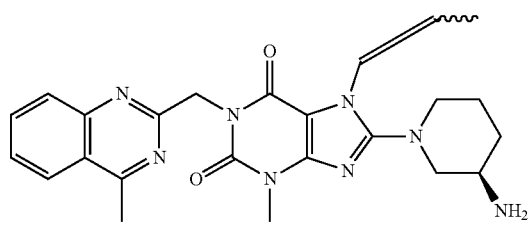

Said impurities are known and recognized in the finished product in an amount of about 0.2%. Therefore there is a need to find new intermediates for the synthesis of Linagliptin and its salts and a process for its preparation with high yield and high chemical purity, without the formation of an isolated salt thereof.

DESCRIPTION OF THE INVENTION

We have now found new intermediates for the synthesis of Linagliptin and its salts and a process for its preparation with high yield and high chemical purity, which involves the use of derivatives of (R)-3-amino-piperidine having a low cost protecting group, which is stable during the reaction with compound (II) and can be removed under mild conditions.

An object of the present invention refers to new intermediates of formula (V) for the synthesis of Linagliptin and its salts:

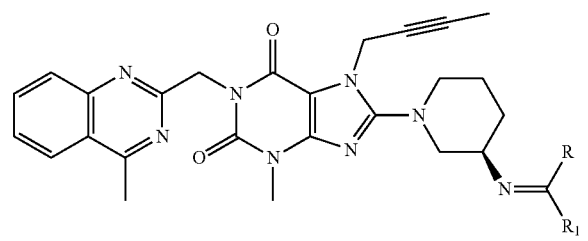

(V)

wherein R and $R_1$, which can be the same or different, are selected from H; straight or branched C1-C6 alkyl; C5-C6 cycloalkyl optionally substituted with C1-C4 alkyl groups; C3-C9 alkenyl; phenyl, naphthyl, heteroaryl optionally substituted with one or more groups selected from straight or branched C1-C6 alkyl, halogens, —$NO_2$, —$OR_2$ groups wherein $R_2$ is selected from H, straight or branched C1-C6 alkyl, optionally substituted benzyl or R and $R_1$ linked together to form an optionally substituted C5 or C6 cycle; preferably R and $R_1$ are selected from hydrogen, methyl, ethyl, propyl, isopropyl, butyl, isobutyl, sec-butyl, tert-butyl, phenyl, benzyl, p-tolyl, p-methoxyphenyl, m-methoxyphenyl, p-nitrophenyl, p-chlorophenyl, 3,4-dimethoxyphenyl, 2-thiophenyl, 2-furanyl, cyclopentyl, cyclohexyl, —CH═CH-Ph, R and $R_1$ are linked together to form a cyclohexane or a 3-methyl or 4-methyl substituted cyclohexane; more preferably R is hydrogen and R1 is phenyl.

Another object of the present invention is a process for the preparation of Linagliptin and its salts, comprising:

(a) the reaction of a compound of formula (II) with a compound of formula (VI) to give compounds of formula (V)

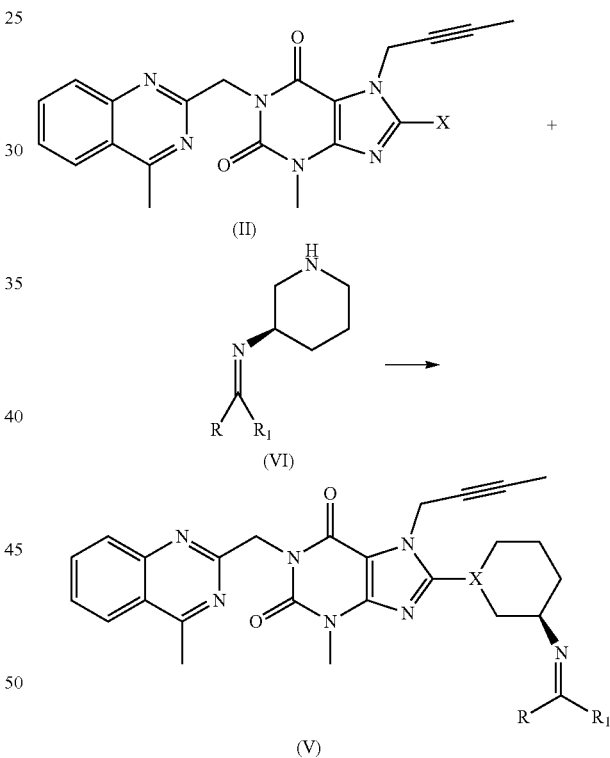

in the presence of a base in a suitable solvent and optionally in the presence of a phase transfer agent, wherein X is an halogen, preferably selected from Cl, Br, I, more preferably Cl or Br, R and $R_1$, which can be the same or different, are selected from H; straight or branched C1-C6 alkyl; C5-C6 cycloalkyl optionally substituted with C1-C4 alkyl groups; C3-C9 alkenyl; phenyl, naphthyl, heteroaryl optionally substituted with one or more groups selected from straight or branched C1-C6 alkyl, halogens, —$NO_2$, —$OR_2$ groups wherein $R_2$ is selected from H, straight or branched C1-C6 alkyl, optionally substituted benzyl or R and $R_1$ linked together to form an optionally substituted C5 or C6 cycle; preferably R and $R_1$ are selected from hydrogen, methyl, ethyl, propyl, isopropyl, butyl, isobutyl, sec-butyl, tert-butyl, phenyl, benzyl, p-tolyl, p-methoxyphenyl, m-methoxyphenyl, p-nitrophenyl, p-chlorophenyl, 3,4-dimethoxyphenyl, 2-thiophenyl, 2-furanyl, cyclopentyl, cyclohexyl, —CH═CH-Ph, R and $R_1$ are linked together to form a cyclohexane or a 3-methyl or 4-methyl substituted cyclohexane; more preferably R is hydrogen and $R_1$ is phenyl;

(b) the deprotection of intermediates of formula (V), optionally isolated, to give Linagliptin and the optional subsequent formation of a salt thereof.

In step (a) the bases are selected from hydroxides, carbonates, bicarbonates and phosphates of alkaline and alkaline earth metals, or mixtures thereof. Preferably the bases are selected from sodium carbonate, potassium carbonate, cesium carbonate, sodium phosphate, potassium phosphate, more preferably potassium carbonate and potassium phosphate.

In step (a) the solvents are apolar or polar aprotic, aromatic, aliphatic, ethers, esters, ketones or mixtures thereof containing an amount of water between 0% and 6%.

Solvents can be selected from acetonitrile, dimethylsulfoxide, sulfolane, N-methylpyrrolidone, dimethylformamide, toluene, xylenes, cumene, cymene, valerolactone, cyclopentyl methyl ether, methyl isobutyl ketone or mixtures thereof containing an amount of water from 0% to 6%, preferably said solvents are selected from toluene, xylene, cumene, cymene, N-methylpyrrolidone or mixtures thereof containing an amount of water from 0% to 6% (v/v), more preferably toluene containing an amount of water from 0% to 6% (v/v) and an amount on N-methylpyrrolidone from 0% to 10% (v/v).

In step (a) the optionally used phase transfer agent is selected from ammonium or tetrasubstituted phosphonium salts.

In step (a) the molar ratio of (II) to (VI) is preferably between 1/1 and 1/1.5.

The compounds of formula (V) obtained in step (a) can be optionally isolated. The optional isolation is preferably carried out by precipitation or crystallization in the presence of a straight or branched C1-C4 alcohol or an ester or an ether or mixtures thereof in the presence of aprotic apolar or polar, aromatic, aliphatic solvents or mixtures thereof.

Preferably the compounds of formula (V) obtained in step (a) are isolated by precipitation or crystallization in methanol or ethyl acetate or isopropyl acetate in the presence of acetonitrile, dimethylsulfoxide, sulfolane, N-methylpyrrolidone, dimethylformamide, toluene, xylenes, cumene, cymene, valerolactone, cyclopentyl methyl ether, methyl isobutyl ketone or mixtures thereof optionally in the presence of methyl-t-butyl ether.

The formation of the compounds of formula (VI) used in step (a) can be carried out by the reaction of (R)-3-aminopiperidine with the compounds of formula (VII), wherein R and R1 have the meanings above reported,

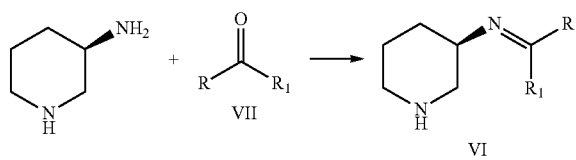

by known procedures or by optionally using an acid catalyst in a suitable solvent or mixture of solvents at a temperature between 20° C. and 150° C., preferably at a temperature between 20° C. and 110° C. Examples of solvents are C2-C6 alcohols, toluene, xylenes, cumene, cymene, valerolactone, cyclopentyl methyl ether, methyl isobutyl ketone or mixtures thereof, preferably ethanol or toluene are used. In the formation reaction of compounds of formula (VI), the acids optionally used, in homogeneous or heterogeneous phase, can be straight or branched C1-C6 carboxylic acids, sulfonic acids, activated silica, alumina, bentonite, Brønsted acids or Lewis acids or mixtures thereof.

Examples of acids are acetic acid, p-toluenesulfonic acid, methanesulfonic acid, propylsulfonic acid, toluene sulfonic acid supported to silica or propyl sulfonic supported to silica; HCl, $TiCl_4$, $BF_3$-etherate, montmorillonite K or mixtures thereof, more preferably HCl or acetic acid are used.

The known procedures include the use of a de-hydrating agent selected from molecular sieves or magnesium sulfate or the use of trialkyl formate or a basic catalyst.

Step (b) is carried out in mild acid or basic conditions. Step (b) can be carried out using an organic aqueous biphasic system in the presence of an acid or, alternatively, an organic system or organic aqueous biphasic system with a base, at a temperature between 0° C. and 30° C.

In the case of an organic aqueous biphasic system in the presence of acid, said acid is selected from straight, branched, cyclic C1-C8 carboxylic acids, preferably acetic acid. Preferably the solvent used in said biphasic system is aromatic, aliphatic, ether, chlorinated and mixtures thereof. Examples of solvents are methylene chloride, cyclopentyl methyl ether, toluene, xylenes, cumene, cymene or mixtures thereof, preferably aromatic solvents are selected from toluene, xylene, cumene, cymene and mixtures thereof, more preferably toluene.

In the case of organic system with a base, said base is preferably selected from T-NH2 amines wherein T is straight or branched C1-C8 alkyl, or an OZ group where Z is H or C1-C6 alkyl; preferably selected from methylamine, ethylamine, triethylamine, n-butylamine, t-butylamine, methoxylamine, ethoxylamine, hydroxylamine and their salts or mixtures thereof; more preferably hydroxylamine or its salts are used.

Preferably in said organic system with a base, the solvent is aromatic, aliphatic, alcoholic, ether, chlorinated and mixtures thereof in the presence of water. Examples of solvents are methylene chloride, methyltetrahydrofuran, cyclopentyl methyl ether, acetonitrile, ethanol, methanol, isopropanol, n-propanol, n-butanol, t-butanol, sec-butanol, toluene, xylenes, cumene, cymene or mixtures thereof, preferably ethanol and aromatic solvents selected from toluene, xylene, cumene, cymene or mixtures thereof are used, more preferably toluene or ethanol or mixtures thereof.

In a preferred embodiment of the invention, in step (a) the base used is potassium carbonate or potassium phosphate, the solvent used is toluene containing a water percentage between 0% and 6% (v/v) and a N-methylpyrrolidone percentage between 0% and 10% (v/v);

The isolation is carried out by precipitation or crystallization in the presence of toluene and methanol, optionally in the presence of methyl-t-butyl ether; in step (b) in the case of an organic aqueous biphasic system in the presence of acid, acetic acid is used and the solvent is toluene or, in the case of an organic system with a base, aqueous hydroxylamine or a salt such as hydroxylamine.HCl or sulfate in the presence of toluene in a mixture with ethanol.

Linagliptin obtained by the process of the invention can then be converted into a specific polymorph or into its pharmacologically acceptable salts through known methods.

Linagliptin obtained according to the process of the invention is characterized by high overall yield (about 80%) and high chemical purity (>99.5%) and in particular with a regioisomer (IV) content lower than 0.04% or absent.

The process of the invention provides Linagliptin containing allene by-products in an amount lower than 0.05% which is much lower than the content of said by-products in the product on the market.

The isolation of the intermediate of formula (V) provides a process characterized by greater efficiency in terms of purity of the final product with respect to the processes known in the art, reducing or even eliminating the content of other impurities.

The method of the present invention overcomes the prior art drawbacks and results surprising for the person skilled in the art that, unlike other protective groups, the removal of the protective group of the compound of formula (V) occurs under mild conditions and does not generate other impurities deriving from the known thermal instability of Linagliptin at acid or basic pH.

Therefore, the invention provides an alternative, improved and sustainable process for producing Linagliptin (I) and its pharmacologically acceptable salts, with high chemical purity and excellent yield, surprisingly without the purification of (I) through transformation in a suitable salt and crystallization of said salt followed by subsequent release of Linagliptin, as disclosed in the processes known in the art.

The process of the invention allows to produce low quantities of waste and to control the content of unwanted byproducts operating in the abovementioned suitable conditions.

A further object of the invention relates to a process for the preparation of Linagliptin as disclosed above, also comprising the preparation of pharmaceutical compositions comprising Linagliptin or a pharmacologically acceptable salt thereof, in mixture with one or more conventional pharmaceutical additives.

In order to better illustrate the invention the following examples are now reported.

ANALYTICAL METHODS

X-Ray Diffraction Analysis—Powder Method (XRPD)

Figure 1:
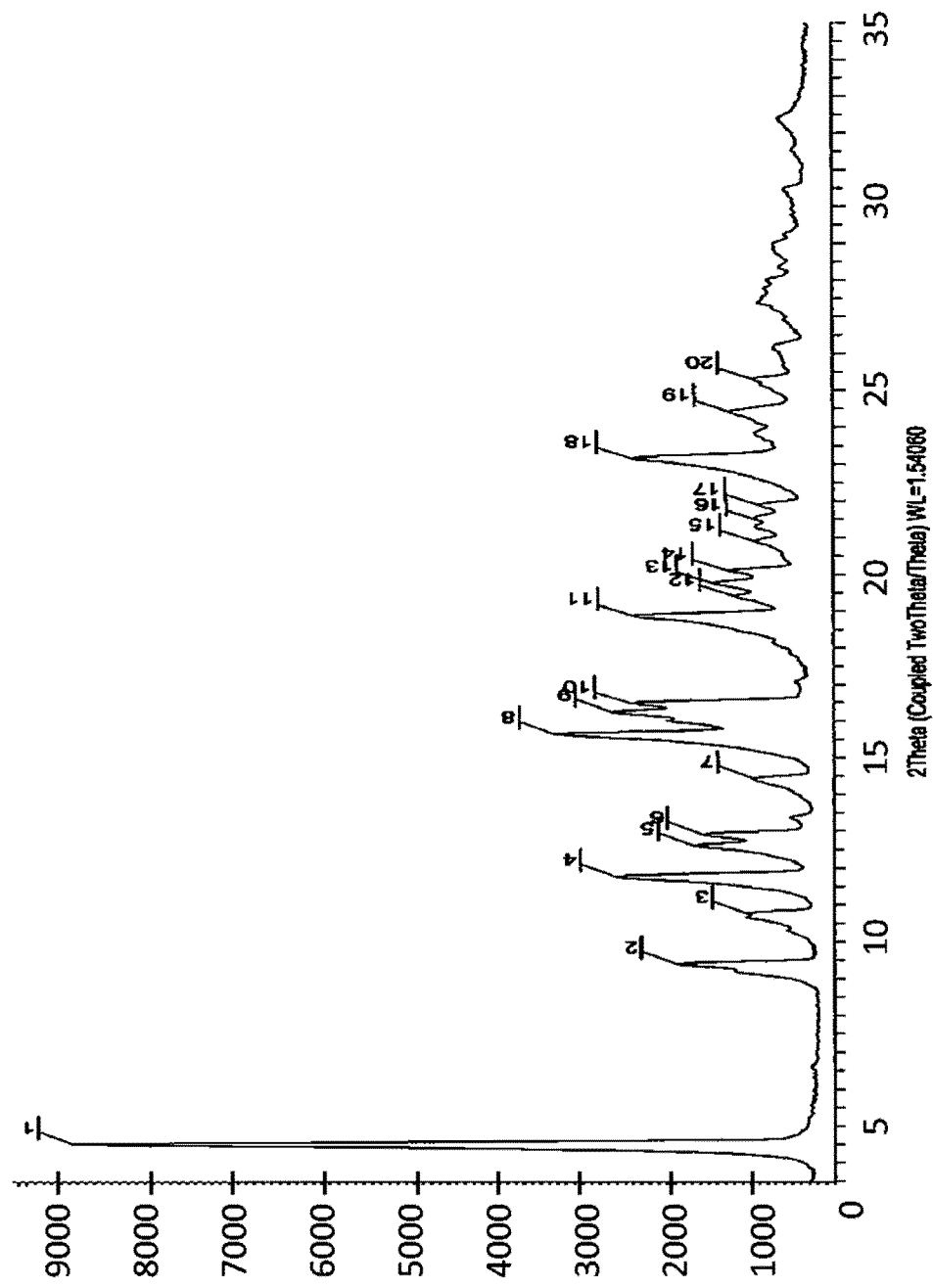
FIG. 1: XRPD diffractogram of compound (V, with R=H and $R_1$=Ph) isolated from MeOH, obtained as in Example 5.

The samples, before being analyzed, were subjected to a mild grinding in agate mortar and then analyzed by X-ray diffraction (powder method—XRPD), with the following instrumental characteristics:

Philips diffractometer model PW1800/10
data processing software X'Pert High Score—v. 2.0a (PANalytical)
Cu Kα radiation ($K\alpha_1$=1.54060 Å $K\alpha_2$=1.54439 Å)
graphite mono-chromator
divergent automatic slide
generator power: 45 Kv, 35 mA
scan interval: 2°-65° 2θ
scan speed (step): 0.02° 2θ/sec
counting time per step: 1.0 sec
Samples were analyzed in the scanning interval: 2°-65° 2θ.

DSC Analysis (Differential Scanning calorimetry)

DSC analysis were performed using the DSC 822e instrument by METTLER TOLEDO. The experiments were carried out with a heating ramp of 5.0° C./min in the range 30-250° C. and with nitrogen flow of 40 ml/min 40 μL aluminum crucibles with perforated lid were used.

IR Analysis (Infrared Spectroscopy)

The IR spectra were recorded using a JASCO FT-IR 460 Plus spectrophotometer. The samples were prepared by grinding about 5 mg of sample with about 500 mg of KBr and analyzed in the range 4000-400 $cm^{-1}$ with a resolution of 4 $cm^{-1}$.

NMR Analysis (Nuclear Magnetic Resonance)

NMR analysis were performed using a Bruker Avance 300 MHz instrument.

Ref. Example A (According to U.S. Pat. No. 7,407,955)

Synthesis of Linagliptin from tert-butyl (R)-(1-(7-(but-2-yn-1-yl)-3-methyl-1-((4-methylquinazolin-2-yl)methyl)-2,6-dioxo-2,3,6,7-tetrahydro-1H-purin-8-yl)piperidin-3-yl)carbamate (BOC-protected Linagliptin)

Under inert atmosphere, 20 g (34.5 mmol) of (R)-1-(4-methyl-quinazolin-2-ylmethyl)-7-(but-2-ynyl)-8-(3-tert-butoxycarbonylamino-piperidin-1-yl)-xanthine and 140 ml of methylene chloride are charged in a round bottom flask. 26.5 ml (345 mmol) of trifluoroacetic acid are slowly added at 0-5° C. The temperature is raised to 20-25° C. and the mixture is kept under stirring, at the same temperature, for 24 hours. The mixture is cooled to 0-5° C. and 200 ml of water are added. After phase separation, to the aqueous phase, maintaining the temperature at 5-10° C., 100 ml of methylene chloride and 27 ml of an aqueous solution of 30% sodium hydroxide are then added (up to a pH of about 10). After separation of the aqueous phase, the organic phase is concentrated under vacuum. To the obtained residue, 83 ml of ethanol are added and the mixture is heated to reflux. The solution is cooled to 20-25° C., and 83 ml of methyl-t-butyl ether are added to the obtained suspension. The mixture is kept under stirring at 20-25° C. for 1 h, then it is cooled to 0-5° C. for 2 h. The solid is filtered, washed with 33 ml of methyl-t-butyl ether at 0-5° C. and dried under vacuum at 45° C. for 16 h to give 7 g of Linagliptin (I) (yield 44% HPLC purity 99.4%).

Ref. Example B (According to U.S. Pat. No. 8,883,805)

Synthesis of Linagliptin from (R)-7-(but-2-yn-1-yl)-8-(3-(1,3-dioxoisoindolin-2-yl)piperidin-1-yl)-3-methyl-1-((4-methylquinazolin-2-yl)methyl)-3,7-dihydro-1H-purine-2,6-dione (Phthalimido-protected Linagliptin)

Method 1:

In a 500 mL flask, 14 g of (R)-7-(but-2-yn-1-yl)-8-(3-(1,3-dioxoisoindolin-2-yl)piperidin-1-yl)-3-methyl-1-((4-methylquinazolin-2-yl)methyl)-3,7-dihydro-1H-purine-2,6-dione (23.2 mmol) and 140 mL of Toluene are charged at 20° C. under inert atmosphere. After heating the suspension to 83° C. in 30 min, 14 mL of Ethanolamine (232.3 mmol) are added dropwise. The solution is maintained at 83° C. for 2 h. Ethanolamine phase is separated from the toluene phase. Ethanolamine is washed with Toluene (2×31 mL) at 20° C. The toluene phases are combined and washed with water (2×62 mL) at 83° C. 160 mL of toluene are distilled under vacuum and methyltertbutyl ether (31 mL) is added at 45° C. allowing the product precipitation. The suspension is cooled to 0° C. in 1 hour and filtered. The solid is washed with methyltertbutyl ether (31 mL) at 0° C. The wet product is dried under vacuum at 45° C. for 16 h (yield 83%; HPLC purity 95.6%).

Method 2

Under inert atmosphere, 14 g of (R)-7-(but-2-yn-1-yl)-8-(3-(1,3-dioxoisoindolin-2-yl)piperidin-1-yl)-3-methyl-1-((4-methylquinazolin-2-yl)methyl)-3,7-dihydro-1H-purine-2,6-dione (23.2 mmol) and 49 mL of tetrahydrofuran at 20° C. are charged into a 250 mL flask. After heating the suspension to 61° C. in 30 min, 3.5 mL of water and 14 mL of ethanolamine (232.3 mmol) are added in sequence. After 3 hours, 9 mL of an aqueous solution of NaOH at 30% (w/v) and 39 mL of water are added at 61° C. After additional 30 min toluene is added (56 mL) and the resulting biphasic solution is stirred for 15 min. The phases are maintained at 61° C. and the aqueous phase is eliminated. The organic phase is washed with water (28 mL) at 61° C. About 60 mL of the organic solvent are distilled under vacuum. Methyl-cyclohexane (14 mL) is added to the remaining solution, heated to 70° C., allowing product crystallization. The suspension is cooled to 0° C. and the product is filtered. The solid is washed with methyl-cyclohexane (42 mL) and subsequently dried under vacuum at 45° C. for 16 h (Yield 78%; HPLC purity 97.5%)

Example 1

Synthesis of (R)-3-(benzylideneamino)piperidine (VI, R=H, R$_1$=Ph)

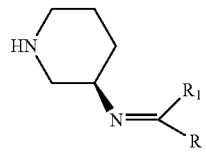

In a 1 L flask 19.1 g (110 mmol) of (R)-3-Aminopiperidine di-hydrochloride and 80 ml of ethanol are charged, under inert atmosphere. 43 ml (132 mmol) of an ethanolic solution of sodium ethylate at 21% are slowly added to the mixture at 20-25° C.; after 2.5 hours, ethanol is distilled under vacuum. 200 ml of toluene are added to the residue and the mixture is heated to 70° C.; then 12.3 ml (121 mmol) of benzaldehyde and 0.5 ml (8.8 mmol) of acetic acid are added and the mixture is kept at 70° C. under vacuum (P=200-300 mbar) until completion of the reaction (using Dean Stark system). The mixture containing the crude compound (VI, R=H, R$_1$=Ph) is used as such for the next step.

Example 2

Synthesis of (R)-3-(benzylideneamino)piperidine (VI, R=H, R$_1$=Ph)

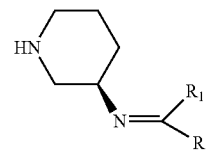

In a 1 L flask, 19.1 g (110 mmol) of (R)-3-Aminopiperidine di-hydrochloride and 80 ml of ethanol are charged under inert atmosphere. 43 ml (132 mmol) of an ethanolic solution of sodium ethylate at 21% are slowly added to the mixture at 20-25° C.; after 2.5 hours, ethanol is distilled under vacuum. 200 ml of toluene are added to the residue and the mixture is heated to 70° C.; then 16 ml (158.8 mmol) of benzaldehyde and 0.5 ml (8.8 mmol) of acetic acid are added and the mixture is kept at 70° C. under vacuum (P=200-300 mbar) until completion of the reaction (using Dean Stark system). The mixture containing the crude compound (VI, R=H, R$_1$=Ph) is used as such for the next step.

Example 3

Synthesis of (R)-3-(benzylideneamino)piperidine (VI, R=H, R$_1$=Ph)

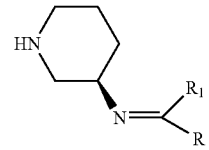

In a 1 L flask, 17.2 g (99.3 mmol) of (R)-3-Aminopiperidine di-hydrochloride and 60 ml of ethanol are charged under inert atmosphere. 38 ml (119.2 mmol) of an ethanolic solution of sodium ethylate at 21% are slowly added to the mixture at 20-25° C.; after 2.5 hours, the ethanol is distilled under vacuum. 150 ml of toluene are added to the residue and the mixture is heated to 70° C.; then 15.1 ml (149 mmol) of benzaldehyde and 0.3 ml (6.6 mmol) of acetic acid are added and the mixture is kept at 70° C. under vacuum (P=200-300 mbar) until the reaction is completed (using system Dean Stark). The mixture containing the crude compound (VI, R=H, R$_1$=Ph) is used as such for the next step.

Example 4

Synthesis of (R)-3-(benzylideneamino)piperidine (VI, R=H, R$_1$=Ph)

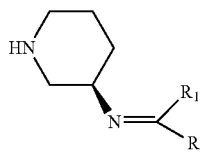

In a 1 L flask, 19 g (110 mmol) of (R)-3-Aminopiperidine di-hydrochloride and 80 ml of ethanol are charged under inert atmosphere. 70.5 ml (189 mmol) of an ethanolic solution of sodium ethylate at 21% are slowly added at 20-25° C. to the mixture; after 2 hours, 12.3 ml (121 mmol) of benzaldehyde are added and the mixture is kept at 20-25° C. until the reaction is completed. The mixture containing the crude compound (VI, R=H, R$_1$=Ph) is used as such for the next step.

Example 5

Synthesis of (R)-8-(3-(benzylideneamino)piperidin-1-yl)-7-(but-2-yn-1-yl)-3-methyl-1-((4-methylquinazolin-2-yl)methyl)-3,7-dihydro-1H-purine-2,6-dione (V, R=H, R$_1$=Ph)

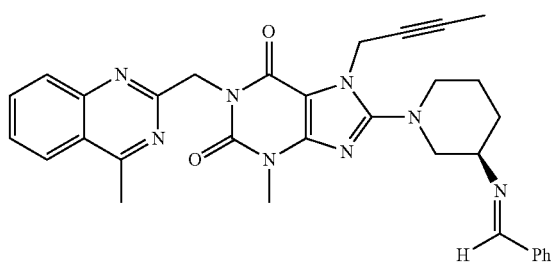 [SMILES: CC#CCn1c(N2CCC[C@@H](/N=C/c3ccccc3)C2)nc2c1c(=O)n(Cc1nc(C)c3ccccc3n1)c(=O)n2C]

To the mixture of the crude compound (VI, R=H, R1=Ph) in toluene obtained from example 1, 40 g (88.2 mmol) of 8-bromo-7-(but-2-yn-1-yl)-3-methyl-1-((4-methylquinazolin-2-yl)methyl)-3,7-dihydro-1H-purine-2,6-dione (II, X=Br), 120 ml of toluene and 24.4 g (176 mmol) of potassium carbonate are added. The mixture is heated to 100° C. until the reaction is completed and subsequently cooled to 50-60° C. The organic phase is washed with 3×120 ml of water and then the mixture is concentrated under vacuum to residue. 120 ml of methanol are added and concentrated under vacuum; the operation is repeated two times. 200 ml of methyl-t-butyl ether are added at 20-25° C. to the obtained suspension, the mixture is heated to 50° C. under stirring and the temperature is maintained for 1 hour, then cooled to 0-5° C. and maintained under stirring for 2 hours. The solid is filtered, washed with 80 ml of methyl-t-butyl ether at 0-5° C. and dried under vacuum at 45° C. to give 45.1 g of (V, R=H, R$_1$=Ph), yield 91.2%.

Figure 2:
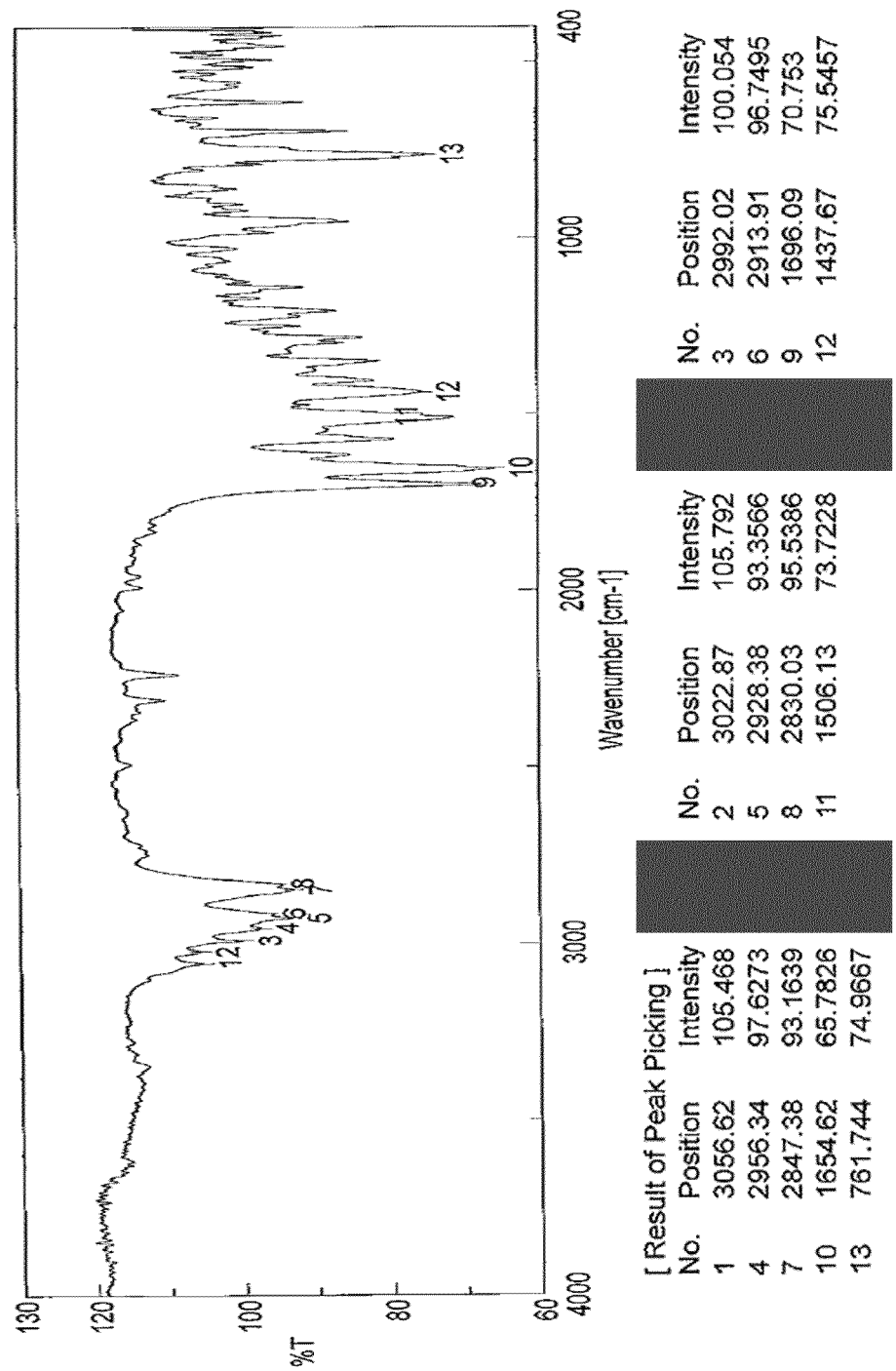
FIG. 2: IR spectrum of compound (V, with R=H and $R_1$=Ph) isolated from MeOH, obtained as in Example 5.
Figure 3:
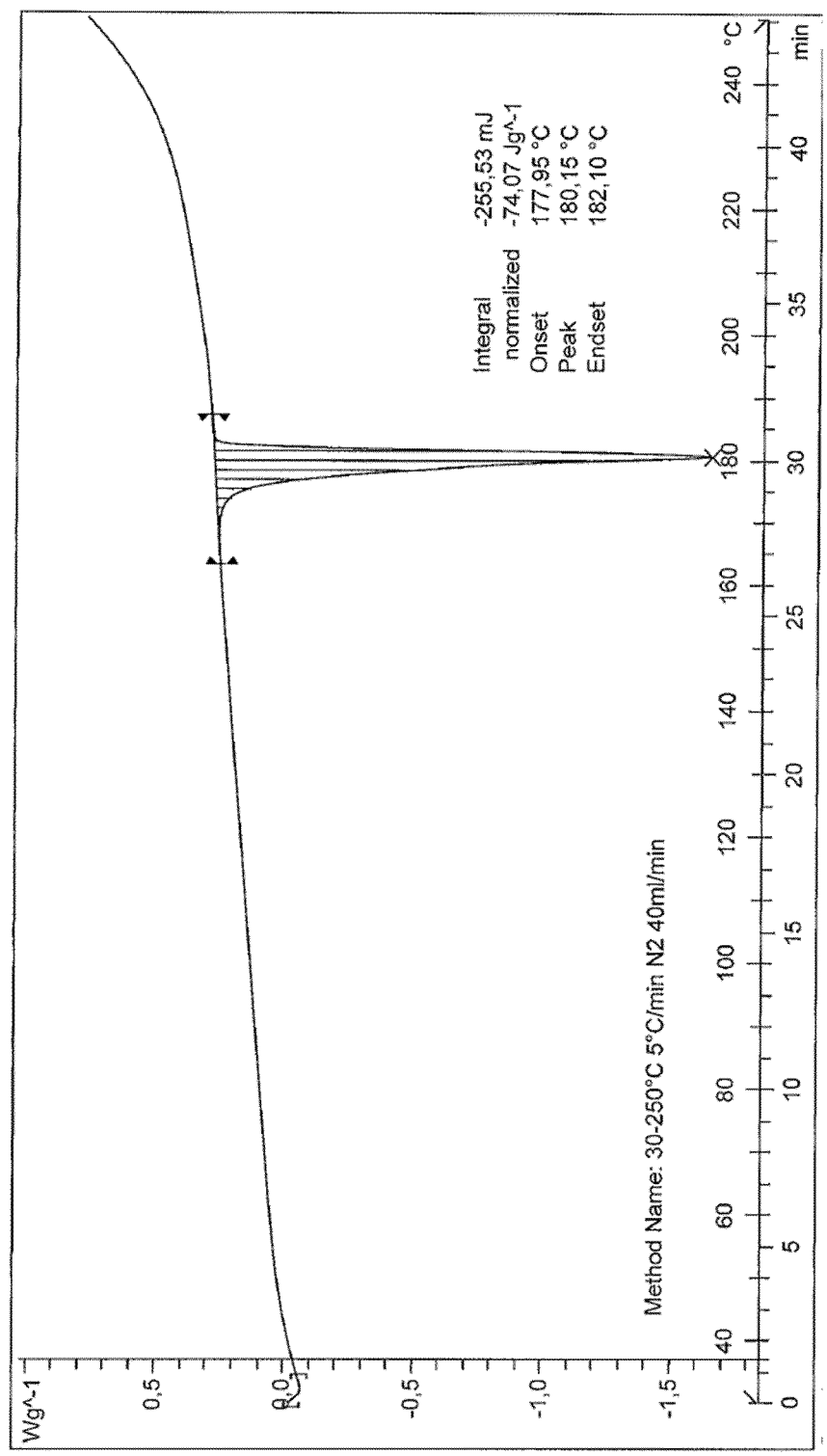
FIG. 3: DSC of compound (V, with R=H and $R_1$=Ph) isolated from MeOH, obtained as in Example 5.

XRPD diffractogram is shown in FIG. 1, IR spectrum is shown in FIG. 2, DSC is shown in FIG. 3.

LC-ESI-MS: 561.3 (M-H$^+$).

$^1$H-NMR (DMSO d$_6$, 300 MHz) (δ in ppm with respect to TMS): 1.72 (3H, bs, CH$_3$), 1.75-2.00 (4H, m); 2.88 (3H, s, CH$_3$); 3.17 e 3.77 (2H, m); 3.23 e 3.80 (2H, m); 3.41 (3H, s, NCH$_3$); 3.60 (1H, m); 4.91 (2H, bs); 5.34 (2H, s); 7.40-7.47 (3H, m); 7.66 (1H, dt, J=8, 1 Hz); 7.76 (2H, m); 7.79 (1H, d, J=8 Hz); 7.90 (1H, dt, J=8.1 Hz); 8.23 (1H, d, J=8 Hz); 8.51 (1H, s).

$^{13}$C-NMR (DMSO d$_6$, 300 MHz) (δ in ppm with respect to TMS, the multiplicity has been derived from spectrum DEPT-135): 3.0 (CH$_3$); 21.5 (CH$_3$); 22.9 (CH$_2$); 29.4 (—NCH$_3$); 31.7 (CH$_2$); 35.6 (CH$_2$); 45.6 (CH$_2$); 49.3 (CH$_2$); 55.2 (CH$_2$); 65.2 (CH); 73.8; 81.2; 103.3; 122.5; 125.6 (CH); 127.1 (CH); 127.9 (CH); 128.6 (CH); 130.7 (CH); 134.0 (CH); 136.1; 147.7; 149.1; 151.0; 153.3; 155.9; 160.9 (CH=N); 161.0; 168.7.

Example 6

Synthesis of (R)-8-(3-(benzylideneamino)piperidin-1-yl)-7-(but-2-yn-1-yl)-3-methyl-1-((4-methylquinazolin-2-yl)methyl)-3,7-dihydro-1H-purine-2,6-dione (V, R=H, R$_1$=Ph)

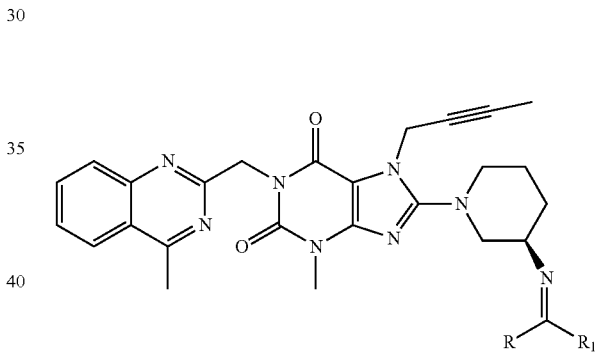

30 g (66.2 mmol) of 8-bromo-7-(but-2-yn-1-yl)-3-methyl-1-((4-methylquinazolin-2-yl)methyl)-3,7-dihydro-1H-purine-2,6-dione (II, X=Br), 90 ml of toluene and 27.5 g (199 mmol) of potassium carbonate are added to the mixture of the crude compound in toluene (VI, R=H, R$_1$=Ph), obtained from example 3. The mixture is heated to 100° C. until the reaction is completed and subsequently cooled to 50-60° C. The organic phase is washed with 3×90 ml of water and then the mixture is concentrated under vacuum to residue. 90 ml of ethyl acetate are added and concentrated under vacuum; the operation is repeated two times. To the obtained suspension, 90 ml of methyl-t-butyl ether at 20-25° C. are added, the mixture is heated to 50° C. under stirring and maintained at the temperature for 1 hour, then cooled to 0-5° C. and kept under stirring for 2 h. The solid is filtered, washed with 60 ml of methyl-t-butyl ether at 0-5° C. and dried under vacuum at 45° C. to give 33.0 g of (V, R=H, R$_1$=Ph), yield 89.0%.

Figure 4:
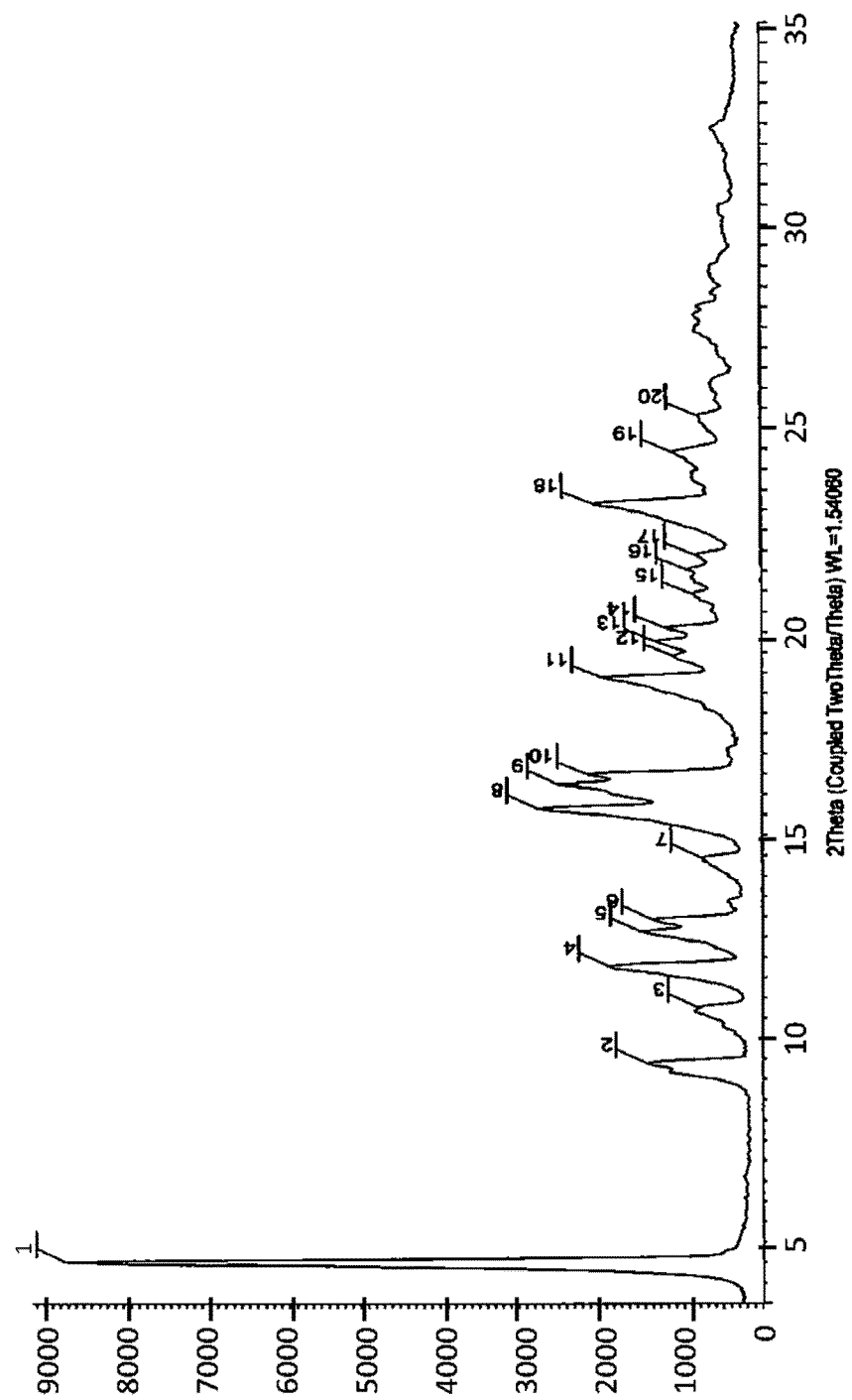
FIG. 4: XRPD diffractogram of compound (V, with R=H and $R_1$=Ph) isolated from AcOEt, obtained as in Example 6.
Figure 5:
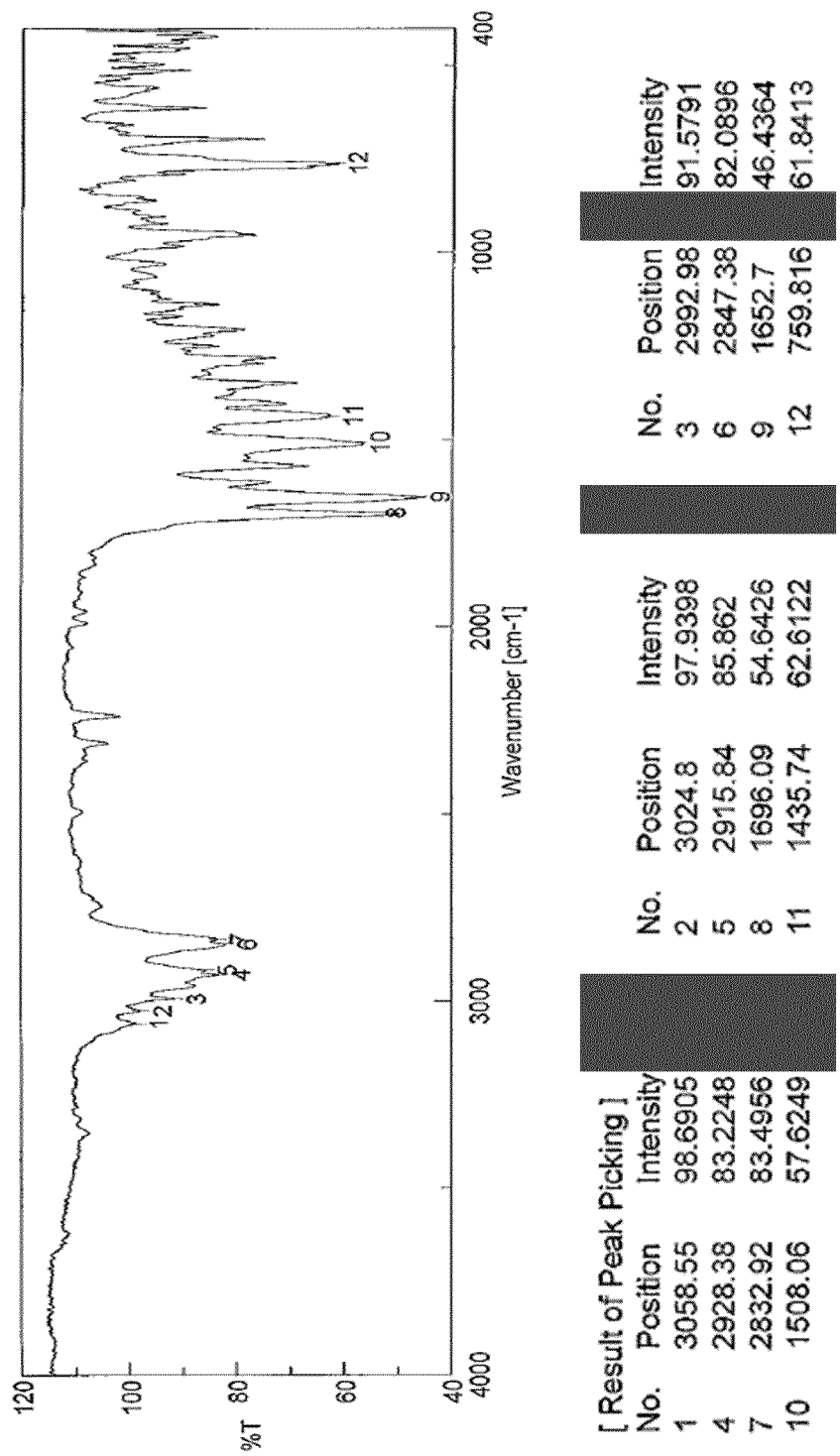
FIG. 5: IR spectrum of compound (V, with R=H and $R_1$=Ph) isolated from AcOEt, obtained as in Example 6.
Figure 6:
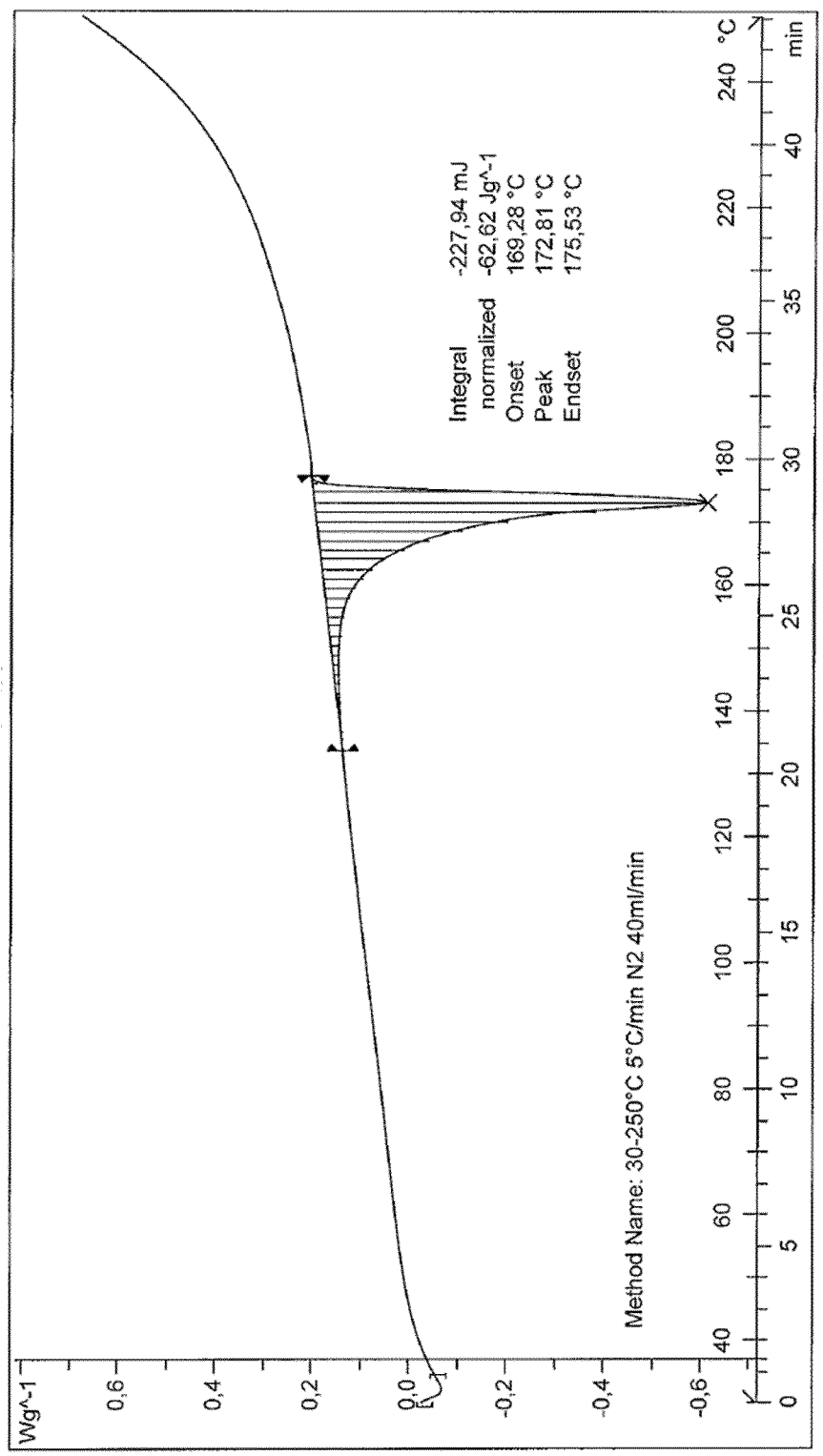
FIG. 6: DSC of compound (V, with R=H and $R_1$=Ph) isolated from AcOEt, obtained as in Example 6.

XRPD diffractogram is shown in FIG. 4, IR spectrum is shown in FIG. 5, DSC is shown in FIG. 6.

Example 7

Synthesis of (R)-8-(3-(benzylideneamino)piperidin-1-yl)-7-(but-2-yn-1-yl)-3-methyl-1-((4-methylquinazolin-2-yl)methyl)-3,7-dihydro-1H-purine-2,6-dione (V, R═H, R$_1$═Ph)

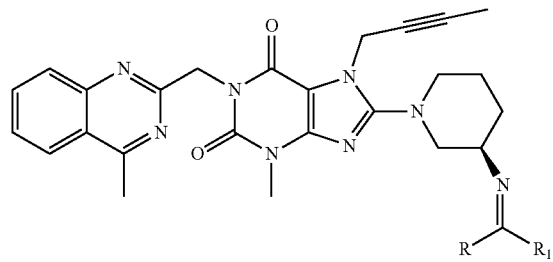

To the mixture of the crude compound (VI, R═H, R1═Ph) in toluene obtained from Example 2, 40 g (88.2 mmol) of 8-bromo-7-(but-2-yn-1-yl)-3-methyl-1-((4-methylquinazolin-2-yl)methyl)-3,7-dihydro-1H-purine-2,6-dione (II, X═Br), 120 ml of toluene and 36.5 g (264 mmol) of potassium carbonate are added. The mixture is heated to 100° C. until the reaction is completed and subsequently cooled to 50-60° C. The organic phase is washed with 3×120 ml of water and then concentrated under vacuum to residue. The mixture containing the crude compound (V, R═H, R$_1$═Ph) is used as such for the next step.

Example 8

Synthesis of (R)-8-(3-(benzylideneamino)piperidin-1-yl)-7-(but-2-yn-1-yl)-3-methyl-1-((4-methylquinazolin-2-yl)methyl)-3,7-dihydro-1H-purine-2,6-dione (V, R═H, R$_1$═Ph)

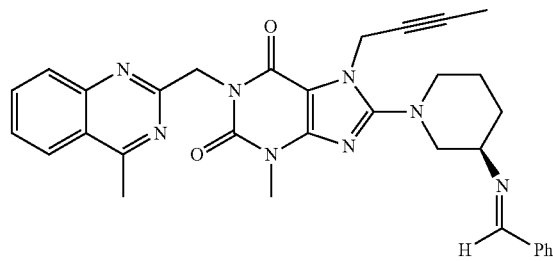 [SMILES: CC#CCn1c(N2CCC[C@@H](/N=C/c3ccccc3)C2)nc2c1c(=O)n(Cc1nc(C)c3ccccc3n1)c(=O)n2C]

The ethanol of the mixture of the crude compound (VI, R═H, R$_1$═Ph) obtained from example 4, is distilled under vacuum. 320 ml of toluene are added to the residue and 120 ml are distilled under vacuum. To the mixture obtained, 40 g (88.2 mmol) of 8-bromo-7-(but-2-yn-1-yl)-3-methyl-1-((4-methylquinazolin-2-yl)methyl)-3,7-dihydro-1H-purine-2,6-dione (II, X═Br), 96 ml of toluene, 56 g (264 mmol) of potassium phosphate and 24 ml of N-methyl pyrrolidone are added. The mixture is heated to 103° C. until the reaction is completed and subsequently cooled to 20-25° C. The organic phase is washed with 3×120 ml of water and then the mixture is concentrated under vacuum to residue. 320 ml of methanol and 20 ml of toluene are added at 40-45° C. than the solution is cooled to 20-25° C. To the obtained suspension, 160 ml of methanol are added and the mixture is heated to 40° C. under stirring and the temperature is maintained for 2 hours, then cooled to 0-5° C. and maintained under stirring for 1 hours. The solid is filtered, washed with 80 ml of methyl-t-butyl ether at 0-5° C. and dried under vacuum at 45° C. to give 44.2 g of (V, R═H, R$_1$═Ph), yield 90.1%.

Example 9

Synthesis of Linagliptin 30 g (80.4 mmol) of (V, R═H, R$_1$═Ph) obtained as in example 4, are charged in a 1 L flask with 120 ml of toluene and 30 ml of ethanol, under an inert atmosphere. 10.6 ml (161 mmol) of a 50% aqueous hydroxylamine solution are slowly added at 20-25° C. and the mixture is kept under stirring, at the same temperature, for 2 h. The organic phase is washed with 150 ml of water, then the organic phase is cooled to 5-10° C. and 210 ml of water and 4.3 ml of glacial acetic acid (up to a pH of about 4.5) are added. After phase separation, the aqueous phase, maintaining the temperature at 5-10° C., is extracted with 150 ml of toluene. 150 ml of toluene and 12.5 ml of an aqueous solution of 30% ammonium hydroxide (up to a pH of about 9.0) are then added to the aqueous phase. The biphasic mixture is heated to 60° C. and after phase separation, the organic phase is concentrated under vacuum. The obtained suspension is cooled to 20-25° C., 120 ml of methyl-t-butyl ether are added and the mixture is heated to 50° C. The mixture is kept under stirring at 50° C. for 1 hour, then cooled at 0-5° C. for 2 hour. The solid is filtered, washed with 60 ml of methyl-t-butyl ether at 0-5° C. and dried under vacuum at 45° C. for 16 hours to obtain 21.8 g of Linagliptin (I) (yield 86%), having chemical purity >99.5% from HPLC analysis and regioisomer (IV) content less than 0.04%

Example 10

Synthesis of Linagliptin 45 g (80.4 mmol) of (V, R═H, R$_1$═Ph) obtained as in example 4, are charged into a 1 L flask, with 180 ml of toluene and 45 ml of ethanol, under inert atmosphere. 40 ml (603 mmol) of a 50% aqueous hydroxylamine solution are slowly added at 20-25° C. and the mixture is kept under stirring, at the temperature, for 2 h. The organic phase is washed with 225 ml of water, then cooled to 5-10° C. and 315 ml of water and 6.7 ml of glacial acetic acid are added (up to pH of about 4.5). After phase separation, the aqueous phase, maintaining the temperature at 5-10° C., is extracted with 225 ml of toluene. Then 225 ml of toluene and 15 ml of an aqueous solution of 30% ammonium hydroxide are added to the aqueous phase (up to pH of about 9.0). The biphasic mixture is heated to 60° C. and after separation of the aqueous phase, the organic phase is concentrated under vacuum. The obtained suspension is cooled to 20-25° C., 180 ml of methyl-t-butyl ether are added and the mixture is heated to 50° C. The mixture is kept under stirring at 50° C. for 1 h, then cooled to 0-5° C. for 2 hours. The solid is filtered, washed with 90 ml of methyl-t-butyl ether at 0-5° C. and dried under vacuum at 45° C. for 16 hours to obtain 32.5 g of Linagliptin (I) (yield 85.5%), having chemical purity >99.5% from HPLC analysis and regioisomer content (IV) lower than 0.04%.

$^1$H-NMR (DMSO d$_6$, 300 MHz) (δ in ppm with respect to TMS): 1.24 (1H, m); 1.40-1.75 (4H, m); 1.78 (3H, bs, CH$_3$); 1.85 (1H, m); 2.71-2.80 (2H, m); 2.87 (3H, s, CH$_3$); 3.02 (1H, m); 3.41 (3H, s, —NCH$_3$); 3.57-3.70 (2H, m); 4.91

(2H, bs); 5.34 (2H, s); 7.65 (1H, t, J=8 Hz); 7.80 (1H, d, J=8 Hz); 7.92 (1H, dt, J=8, 1 Hz); 8.21 (1H, d, J=8 Hz).

$^{13}$C-NMR (DMSO d$_6$, 300 MHz) (δ in ppm with respect to TMS, the multiplicity has been derived from spectrum DEPT-135): 3.0 (CH$_3$); 21.5 (CH$_3$); 23.3 (CH$_2$); 29.3 (—NCH$_3$); 33.3 (CH$_2$); 35.5 (CH$_2$); 45.6 (CH$_2$); 47.3 (CH); 49.5 (CH$_2$); 57.7 (CH$_2$); 73.8; 81.1; 103.2; 122.5; 125.6 (CH); 127.0 (CH); 127.9 (CH); 134.0 (CH); 147.8; 149.1; 151.0; 153.3; 156.2; 161.0; 168.7

Example 11

Synthesis of Linagliptin 20 g (35.8 mmol) of compound (V, R=H, R$_1$=Ph) obtained as in the example 4, 53 g (501 mmol) of sodium carbonate, 18.7 g (268.5 mmol) of hydroxylamine HCl and 150 ml of dichloromethane, are charged into a 250 ml flask, under inert atmosphere at 20-25° C. The mixture is kept under stirring, at the temperature, for 3 hours. The organic phase is washed with 150 ml of water, then it is cooled to 5-10° C. and 150 ml of water and 5.8 ml of 30% hydrochloric acid solution are added (up to a pH of about 2). After separation of the organic phase, maintaining the temperature at 5-10° C., 100 ml of dichloromethane and 17.4 ml of an aqueous solution of 30% sodium hydroxide (up to a pH of about 10) are added to the aqueous phase. After phase separation, the organic phase is concentrated under vacuum to residue and used as such for the crystallization of Linagliptin (yield 44%).

Example 12

Synthesis of Linagliptin

To the residue of the crude compound (VI, R=H, R$_1$=Ph) obtained as in Example 6, 200 ml of toluene and 50 ml of ethanol are added, under inert atmosphere. 44 ml (662 mmol) of a 50% aqueous hydroxylamine solution are slowly added at 20-25° C. and the mixture is maintained under stirring at the same temperature, for 19 hours. The organic phase is washed with 250 ml of water, then the organic phase is cooled to 5-10° C. and 345 ml of water and 8.1 ml of glacial acetic acid (up to a pH of about 4.5) are added. After phase separation, the aqueous phase, maintaining the temperature at 5-10° C., is extracted with 250 ml of toluene. Then 250 ml of toluene and 17.4 ml of an aqueous solution of 30% ammonium hydroxide (up to a pH of about 9.0) are added to the aqueous phase. The biphasic mixture is heated to 60° C. and after separation of the aqueous phase, the organic phase is concentrated under vacuum. The obtained suspension is cooled to 20-25° C., 200 ml of methyl-t-butyl ether are added and the mixture is heated to 50° C. The mixture is kept under stirring at 50° C. for 1 hour, then it is cooled at 0-5° C. for 2 hours. The solid is filtered, washed with 100 ml of methyl-t-butyl ether at 0-5° C. and dried under vacuum at 45° C. for 16 hours to give 34.95 g of Linagliptin (I) (84% yield), having chemical purity 78.2% from HPLC analysis, regioisomer content (IV) lower than 0.04% and allenes content lower than 0.05%.

Example 13

Synthesis of Linagliptin 10 g (17.9 mmol) of compound (V, R=H, R$_1$=Ph) obtained as in example 4 and 75 ml of toluene are charged into a 250 ml flask under inert atmosphere. 17.8 ml (179 mmol) of butylamine are slowly added to the mixture at 20-25° C. and kept under stirring, at the same temperature, for 48 hours. The obtained solid is filtered and washed with 10 ml of toluene, then dried under vacuum at 65° C. for 16 hours to give 3.9 g of (I) (yield 46%).

Example 14

Synthesis of Linagliptin 10 g (17.9 mmol) of compound (V, R=H, R$_1$=Ph) obtained as in the example 4, 50 ml of acetonitrile and 25 ml of toluene, are charged into a 250 ml flask under inert atmosphere. 10.1 ml (107.4 mmol) of a 33% ethanolic solution of methylamine are slowly added at 20-25° C. The mixture is heated to 75° C. and is kept under stirring, at the temperature, for 8 hours. The obtained solution is concentrated under vacuum to residue and 50 ml of dichloromethane and 50 ml of water are added. After the separation of the aqueous phase, the organic phase is cooled to 5-10° C. and 50 ml of water and 3.5 ml of 37% hydrochloric acid are added (up to a pH of about 2). After separation of the organic phase, maintaining the temperature at 5-10° C., 50 ml of dichloromethane and 10.5 ml of an aqueous solution of 30% sodium hydroxide (up to a pH of about 10) are added to the aqueous phase. After phase separation, the organic phase is concentrated under vacuum to residue and used as such for the crystallization of Linagliptin (yield 85.7%).

Example 15

Synthesis of Linagliptin 10 g (17.9 mmol) of compound (V, R=H, R$_1$=Ph) obtained as in example 4, 40 ml of toluene and 10 ml of ethanol, are charged into a 250 ml flask under inert atmosphere. 36.5 ml (134.3 mmol) of a 25% aqueous solution of methoxylamine.HCl are slowly added to the solution at 20-25° C. and the mixture is kept under stirring, at the same temperature, for 40 hours. To the suspension thus obtained, 50 ml of water are added. The obtained solid is filtered and washed with 10 ml of toluene, then dried under vacuum at 65° C. for 16 hours to give 4.5 g of (I) (yield 53%).

Example 16

Synthesis of Linagliptin 10 g (17.9 mmol) of compound (V, R=H, R$_1$=Ph) obtained as in example 4, 50 ml of toluene and 50 ml of water, are charged into a 250 ml flask under inert atmosphere. 10.2 ml (178.6 mmol) of glacial acetic acid are slowly added to the suspension at 5-10° C. and the mixture is kept under stirring, at the same temperature, for 6 hours. After separation of the upper phase, maintaining the temperature at 5-10° C., the aqueous phase is washed with 50 ml of toluene, which is discarded. To the aqueous phase, 50 ml of toluene and 23 ml of an aqueous solution of 30% ammonium hydroxide (up to a pH of about 9.0) are then added. The biphasic mixture is heated to 60° C. and, after separation of the aqueous phase, the organic phase is concentrated under vacuum. The obtained suspension is cooled to 20-25° C., 40 ml of methyl-t-butyl ether are added and the mixture is heated to 60° C. The mixture is kept under stirring at 60° C. for 1 hour, then cooled to 0-5° C. and kept under stirring for 2 hours. The solid is filtered, washed with 20 ml of methyl-t-butyl ether at 0-5° C. and dried under vacuum at 45° C. for 16 hour to give 6.7 g of Linagliptin (yield 79.7%).

Example 17

Synthesis of Linagliptin 40 g (71 mmol) of (V) (R=H, R$_1$=Ph) obtained as in example 8, are charged into a 1 L flask, with 160 ml of toluene and 40 ml of ethanol, under inert atmosphere. 6.6 ml (107 mmol) of a 50% aqueous hydroxylamine solution are slowly added at 20-25° C. and the mixture is kept under stirring, at the same temperature, for 2 h. The organic phase is washed with 200 ml of water, then cooled to 15° C. and 240 ml of water and 5.7 ml of glacial acetic acid are added (up to a pH of about 4.5). After phase separation, the aqueous phase, maintaining the temperature at 15° C., is extracted with 200 ml of toluene. Then 200 ml of toluene and 18.9 ml of an aqueous solution of 30% ammonium hydroxide are added to the aqueous phase (up to a pH of about 9.5). The biphasic mixture is heated to 60° C. and after separation of the aqueous phase, the organic phase is concentrated under vacuum. The obtained suspension is cooled to 20-25° C., 160 ml of methyl-t-butyl ether are added and the mixture is heated to 60° C. The mixture is kept under stirring at 60° C. for 2 hours, then cooled to 20-25° C. The solid is filtered, washed with 80 ml of methyl-t-butyl ether at 20-25° C. and dried under vacuum at 60° C. for 16 hours to obtain 30 g of Linagliptin (I) (yield 89.9%), having chemical purity >99.5% from HPLC analysis, regioisomer content (IV) lower than 0.04% and allenes content lower than 0.05%.

Example 18

Figure 7:
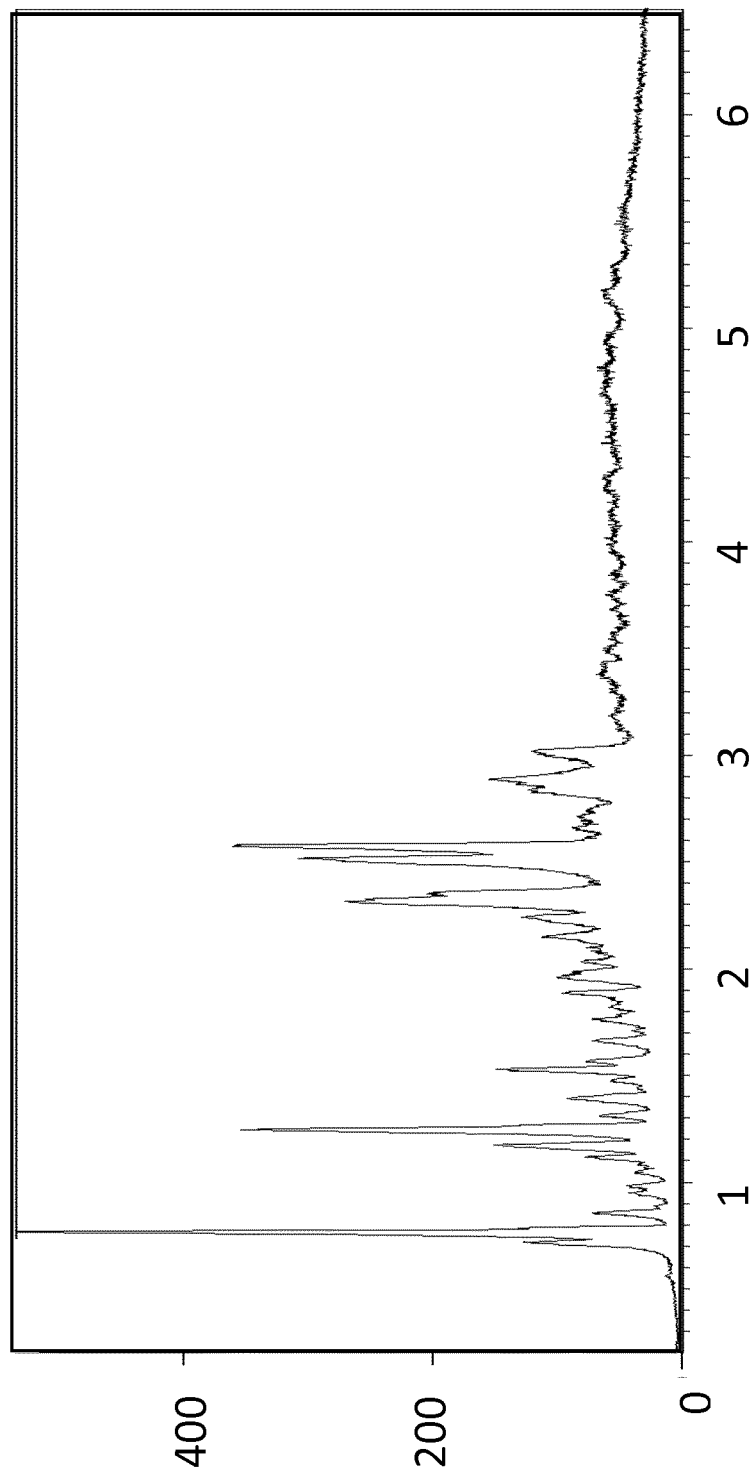
FIG. 7: XRPD diffractogram of Linagliptin obtained according to example 18, mixture of polymorphic forms A/B.

Crystallization of Linagliptin 30 g (63.5 mmol) of (I) obtained according to example 9 and 150 ml of ethanol, under inert atmosphere, are charged into a 500 ml flask. The suspension is heated to reflux, until complete dissolution. Then the solution is cooled to 20° C. in 1 hour, observing precipitation of the product at 20-25° C. 150 ml of methyl-t-butyl ether are then added and the obtained suspension is further cooled to 0-5° C. and kept under stirring for 2 hours. The solid is filtered, washed with 60 ml of methyl-t-butyl ether at 0-5° C. and dried under vacuum at 45° C. for 16 hours to give 25.4 g of (I) (84.5% yield), having chemical purity >99.5% from HPLC analysis and having the XRPD diffractogram reported in FIG. 7 (mixture polymorphic forms A and B)

Example 19

Crystallization of Linagliptin

Figure 8:
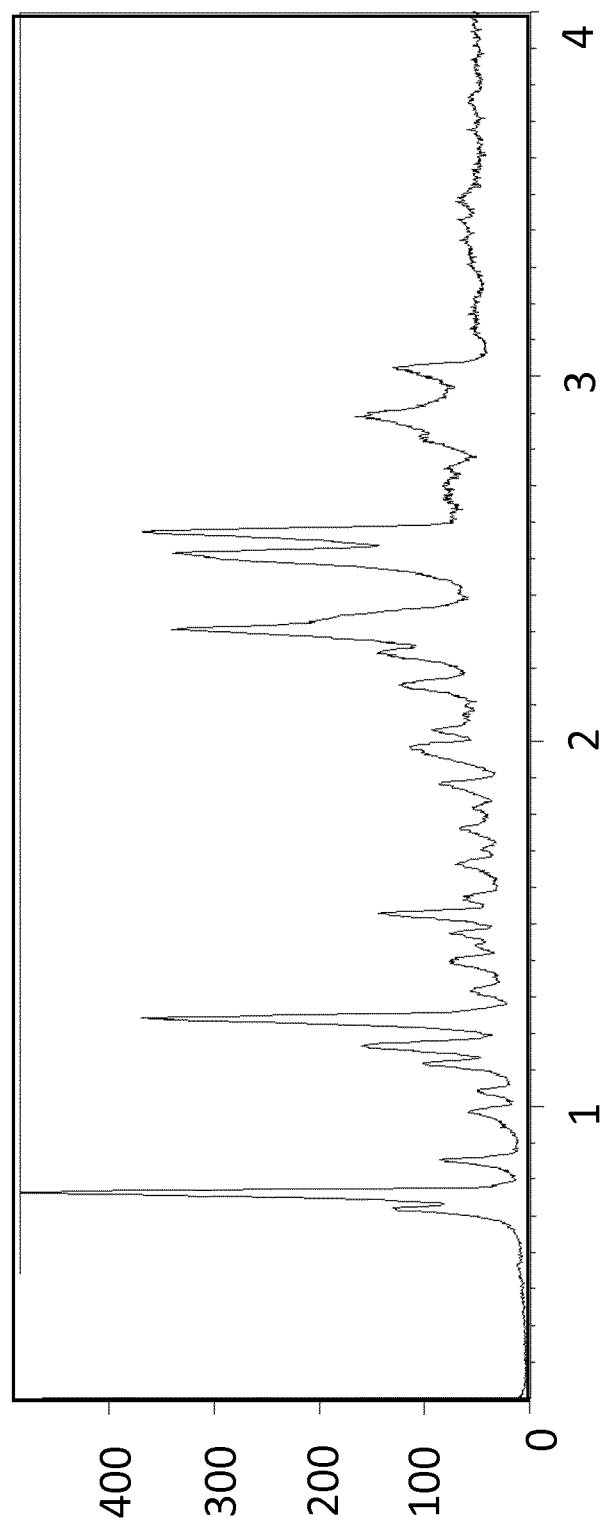
FIG. 8: XRPD diffractogram of Linagliptin obtained according to example 18, polymorphic form A

Under inert atmosphere, 30 g (63.5 mmol) of (I) obtained according to example 9 and 150 ml of ethanol are charged into a 500 ml flask. The suspension is heated to reflux, until complete dissolution. Then the solution is cooled to 20° C. in 1 hour, observing precipitation of the product at 20-25° C. 150 ml of methyl-t-butyl ether are then added and the obtained suspension is kept under stirring for 2 hours. The solid is filtered, washed with 60 ml of methyl-t-butyl ether and dried under vacuum at 45° C. for 16 hours to give 25.4 g of (I) (84.0% yield), having chemical purity >99, 5% from HPLC analysis and having the XRPD diffractogram shown in FIG. 8 (Polymorphic form A).

Examples 20-23

Synthesis of Compounds of Formula VI

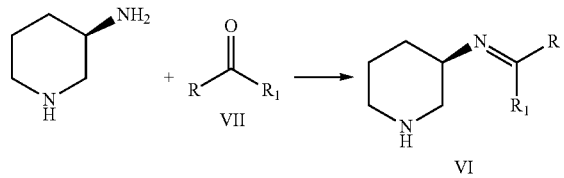

According to the procedure of example 4, maintaining the same molar ratio between the reactants and using 7.16 g (41 mmol) of (R)-3-Aminopiperidine di-hydrochloride, the carbonyl compounds of formula (VII) shown in the table 1 have been used to obtain the respective compounds of formula (VI):

TABLE 1

| Example | Compound VII | Compound VI |
| --- | --- | --- |
| 20 | 4-methyl-benzaldehyde | (R)-1-(4-methylphenyl)-N-(piperidin-3-yl) methanimine |
| 21 | 4-nitro-benzaldehyde | (R)-1-(4-nitrophenyl)-N-(piperidin-3-yl) methanimine |
| 22 | Cinnamaldehyde | 3-phenyl-N-((R)-piperidin-3-yl) prop-2-en-1-imine |
| 23 | Cyclohexanecarbaldehyde | (R)-1-cyclohexyl-N-(piperidin-3-yl) methanimine |

Example 24

Synthesis of (R)-7-(but-2-yn-1-yl)-8-(3-((4-methylibenzylidene)amino)piperidin-1-yl)-3-methyl-1-((4-methylquinazolin-2-yl)methyl)-3,7-dihydro-1H-purine-2,6-dione

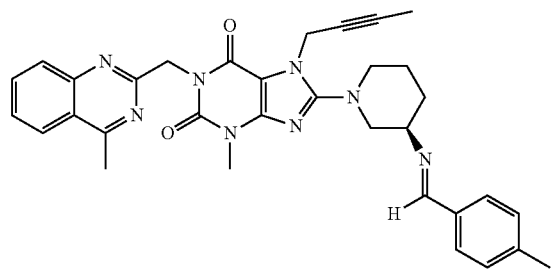 [SMILES: CC#CCn1c(N2CCC[C@@H](/N=C/c3ccc(C)cc3)C2)nc2c1c(=O)n(Cc1nc(C)c3ccccc3n1)c(=O)n2C]

The ethanol of the mixture of the crude compound (VI, R=H, R$_1$=4-Me-Ph) is distilled under vacuum. 120 ml of toluene are added to the residue and 45 ml are distilled under vacuum. To the obtained mixture, 15 g (33 mmol) of 8-bromo-7-(but-2-yn-1-yl)-3-methyl-1-((4-methylquinazolin-2-yl)methyl)-3,7-dihydro-1H-purine-2,6-dione (II, X=Br), 36 ml of toluene, 21.1 g (99 mmol) of potassium phosphate and 9 ml of N-methyl pyrrolidone are added. The mixture is heated to 103° C. until the reaction is completed and subsequently cooled to 20-25° C. The organic phase is washed with 3×45 ml of water and then the mixture is concentrated under vacuum to residue. 120 ml of methanol and 8 ml of toluene are added at 40-45° C. than the solution is cooled to 20-25° C. To the obtained suspension, 60 ml of methanol are added and the mixture cooled to 0-5° C. and maintained under stirring for 1 hours. The solid is filtered, washed with 30 ml of methyl-t-butyl ether at 0-5° C. and dried under vacuum at 45° C. to give 10.3 g of (V, R=H, $R_1$=4-Me-Ph), yield 54.7%.

LC-ESI-MS: 575.1 (M-H$^+$).

$^1$H-NMR (DMSO, 300 MHz) (δ in ppm with respect to TMS): 1.71 (3H, bs,), 1.75-2.00 (4H, m); 2.32 (3H, s, —CH$_3$); 2.86 (3H, s, —CH$_3$); 3.10-3.26 (2H, m); 3.40 (3H, s, —NCH$_3$); 3.55 (1H, m); 3.76 (2H, m); 4.91 (2H, bs); 5.34 (2H, s); 7.23 e 7.63 (4H, J=8 Hz); 7.65 (1H, m); 7.78 (1H, d, J=8 Hz); 7.88 (1H, dt, J=8, 1 Hz); 8.20 (1H, d, J=8 Hz); 8.43 (1H, s, —CH=N).

$^{13}$C-NMR (DMSO, 300 MHz) (δ in ppm with respect to TMS, the multiplicity has been derived from spectrum DEPT-135): 3.0 (CH$_3$); 21.0 (CH$_3$); 21.5 (CH$_3$); 23.0 (CH$_2$); 29.4 (—NCH$_3$); 31.8 (CH$_2$); 35.6 (CH$_2$); 45.6 (CH$_2$); 49.3 (CH$_2$); 55.3 (CH$_2$); 65.1 (CH); 73.8; 81.2; 103.3; 122.5; 125.6 (CH); 127.0 (CH); 127.8 (CH); 127.9 (CH); 129.1 (CH); 133.5; 134.0 (CH); 140.6; 147.6; 149.0; 150.9; 153.2; 155.8; 160.7 (CH=N); 161.0; 168.7.

Example 25

Synthesis of (R)-7-(but-2-yn-1-yl)-3-methyl-1-((4-methyilquinazolin-2-yl)methyl)-8-(3-((4-nitrobenzyliden)amino)piperidin-1-yl)-3,7-dihydro-1H-purine-2,6-dione

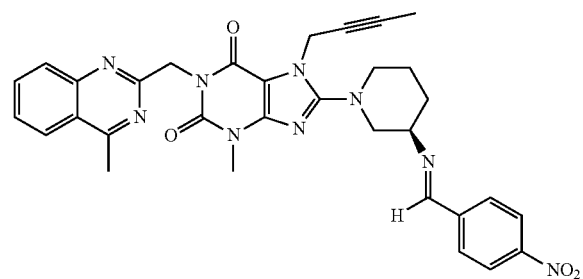 [SMILES: CC#CCn1c(N2CCC[C@@H](/N=C/c3ccc([N+](=O)[O-])cc3)C2)nc2c1c(=O)n(Cc1nc(C)c3ccccc3n1)c(=O)n2C]

The ethanol of the mixture of the crude compound (VI, R=H, $R_1$=4-NO$_2$-Ph) is distilled under vacuum. 120 ml of toluene are added to the residue and 45 ml are distilled under vacuum. To the obtained mixture, 15 g (33 mmol) of 8-bromo-7-(but-2-yn-1-yl)-3-methyl-1-((4-methylquinazolin-2-yl)methyl)-3,7-dihydro-1H-purine-2,6-dione (II, X=Br), 36 ml of toluene, 21.1 g (99 mmol) of potassium phosphate and 9 ml of N-methyl pyrrolidone are added. The mixture is heated to 103° C. until the reaction is completed and subsequently cooled to 20-25° C. The organic phase is washed with 3×45 ml of water and then the mixture is concentrated under vacuum to residue. 150 ml of dichloromethane are added and the solution is concentrated under vacuum to give 19.0 g of crude solid (V, R=H, $R_1$=4-NO$_2$-Ph), yield 95.5%.

LC-ESI-MS: 606.1 (M-H$^+$).

$^1$H-NMR (DMSO d$_6$, 300 MHz) (δ in ppm with respect to TMS): 1.72 (3H, bs, CH$_3$), 1.75-2.00 (4H, m); 2.86 (3H, s, CH$_3$); 3.17 e 3.76 (2H, m); 3.25 e 3.80 (2H, m); 3.40 (3H, s, NCH$_3$); 3.67 (1H, m); 4.90 (2H, bs); 5.33 (2H, s); 7.64 (1H, m); 7.78 (1H, d, J=8 Hz); 7.88 (1H, dt, J=8, 1 Hz); 8.00 e 8.28 (4H, J=8 Hz); 8.21 (1H, d, J=8 Hz); 8.65 (1H, s, —CH=N).

$^{13}$C-NMR (DMSO d$_6$, 300 MHz) (δ in ppm with respect to TMS, the multiplicity has been derived from spectrum DEPT-135): 3.0 (CH$_3$); 21.5 (CH$_3$); 22.8 (CH$_2$); 29.3 (—NCH$_3$); 31.5 (CH$_2$); 35.5 (CH$_2$); 45.6 (CH$_2$); 49.3 (CH$_2$); 55.0 (CH$_2$); 65.1 (CH—B); 73.8; 81.2; 103.3; 122.5; 123.8 (CH); 125.6 (CH); 127.1 (CH); 127.8 (CH); 128.9 (CH); 133.9 (CH); 141.5; 147.6; 148.6; 149.0; 150.9; 153.2; 155.8; 159.5 (CH=N); 161.0; 168.7.

Example 26

Synthesis of 7-(but-2-yn-1-yl)-3-methyl-1-((4-methylquinazolin-2-yl)methyl)-8-((R)-3-(((1E,2E)-3-phenylallylidene)amino)piperidin-1-yl)-3,7-dihydro-1H-purine-2,6-dione

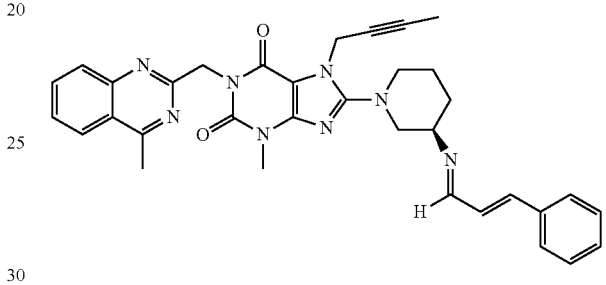

The ethanol of the mixture of the crude compound (VI, R=H, $R_1$=(CH=CH-Ph)) is distilled under vacuum. 120 ml of toluene are added to the residue and 45 ml are distilled under vacuum. To the obtained mixture, 15 g (33 mmol) of 8-bromo-7-(but-2-yn-1-yl)-3-methyl-1-((4-methylquinazolin-2-yl)methyl)-3,7-dihydro-1H-purine-2,6-dione (II, X=Br), 36 ml of toluene, 21.1 g (99 mmol) of potassium phosphate and 9 ml of N-methyl pyrrolidone are added. The mixture is heated to 103° C. until the reaction is completed and subsequently cooled to 20-25° C. The organic phase is washed with 3×45 ml of water and then the mixture is concentrated under vacuum to residue. 150 ml of dichloromethane are added and the solution is concentrated under vacuum. The obtained solid is suspended in 150 ml of diethyl ether at 20-25° C. and maintained under stirring for 4 hours. The solid is filtered, washed with 30 ml of diethyl ether at 20-25° C. and dried under vacuum at 45° C. to give 10.9 g (V, R=H, $R_1$=CH=CH-Ph), yield 56.5%.

LC-ESI-MS: 587.1 (M-H$^+$).

$^1$H-NMR (DMSO, 300 MHz) (δ in ppm with respect to TMS): 1.75 (3H, bs), 1.60-2.00 (4H, m); 2.86 (3H, s, —CH$_3$); 3.10 e 3.75 (2H, m); 3.15 e 3.75 (2H, m); 3.35 (1H, m); 3.40 (3H, s, —NCH$_3$); 4.89 (2H, bs); 5.34 (2H, s); 6.93 (1H, dd, J=16, 8 Hz); 7.13 (1H, d, J=16 Hz); 7.59 e 7.40 (5H, m); 7.64 (1H, m); 7.79 (1H, d, J=8 Hz); 7.89 (1H, t, J=8 Hz); 8.22 (2H, d, J=8 Hz).

$^{13}$C-NMR (DMSO, 300 MHz) (δ in ppm with respect to TMS, the multiplicity has been derived from spectrum DEPT-135): 3.0 (CH$_3$); 21.5 (CH$_3$); 23.1 (CH$_2$); 29.4 (—NCH$_3$); 31.8 (CH$_2$); 35.6 (CH$_2$); 45.6 (CH$_2$); 49.3 (CH$_2$); 55.2 (CH$_2$); 65.3 (CH); 73.8; 81.2; 103.3; 122.5; 125.6 (CH); 127.0 (CH); 127.2 (CH); 127.8 (CH); 127.9 (CH); 128.1 (CH); 128.5 (CH); 128.8 (CH); 129.1 (CH); 134.0 (CH); 135.5; 141.8 (CH); 147.6; 149.0; 150.9; 153.2; 155.7; 161.0; 162.5 (CH=N); 168.7.

Example 27

Synthesis of (R)-7-(but-2-yn-1-yl)-8-(3-((ciclohexylmethylen)amino)piperidin-1-yl)-3-methyl-1-((4-methyilquinazolin-2-yl)methyl)-3,7-dihydro-1H-purin-2,6-dione

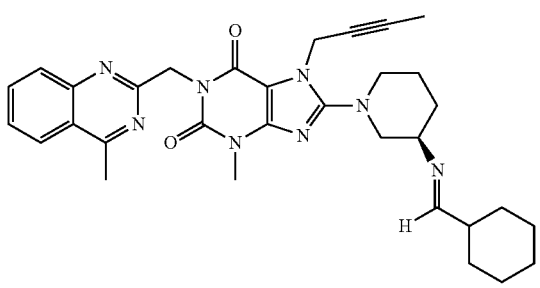 [SMILES: CC#CCn1c(N2CCC[C@@H](/N=C/C3CCCCC3)C2)nc2c1c(=O)n(Cc1nc(C)c3ccccc3n1)c(=O)n2C]

The ethanol of the mixture of the crude compound (VI, R=H, $R_1$=Cyclohexyl) is distilled under vacuum. 120 ml of toluene are added to the residue and 45 ml are distilled under vacuum. To the obtained mixture, 15 g (33 mmol) of 8-bromo-7-(but-2-yn-1-yl)-3-methyl-1-((4-methylquinazolin-2-yl)methyl)-3,7-dihydro-1H-purine-2,6-dione (II, X=Br), 36 ml of toluene, 21.1 g (99 mmol) of potassium phosphate and 9 ml of N-methyl pyrrolidone are added. The mixture is heated to 103° C. until the reaction is completed and subsequently cooled to 20-25° C. The organic phase is washed with 3×45 ml of water and then the mixture is concentrated under vacuum to residue. 120 ml of methanol are added at 40-45° C. than the solution is cooled to 20-25° C. To the obtained suspension, 60 ml of methanol are added and the mixture cooled to 0-5° C. and maintained under stirring for 1 hours. The solid is filtered, washed with 30 ml of methyl-t-butyl ether at 0-5° C. and dried under vacuum at 45° C. to give 12 g of (V, R=H, $R_1$=Cyclohexyl), yield 64.2%.

LC-ESI-MS: 567.1 (M-H⁺).

$^1$H-NMR (CDCl$_3$, 300 MHz) (δ in ppm with respect to TMS): 1.76 (3H, bs, CH$_3$), 1.15-2.00 (14H, m); 2.18 (1H, m); 2.86 (3H, s, —CH$_3$); 3.26 (1H, m); 3.54 (3H, s, —NCH$_3$); 3.08 e 3.70 (2H, m); 3.15 e 3.65 (2H, m); 4.86 (2H, bs); 5.56 (2H, s); 7.49 (1H, t, J=8 Hz); 7.73 (1H, t, J=8 Hz); 7.82 (1H, d, J=8 Hz); 7.98 (1H, d, J=8 Hz); 7.84 (1H, d, J=5.5 Hz, —CH=N).

$^{13}$C NMR (CDCl$_3$, 300 MHz) (δ in ppm with respect to TMS, the multiplicity has been derived from spectrum DEPT-135): 3.5 (CH$_3$); 21.6 (CH$_3$); 23.6 (CH$_2$); 25.2 (CH$_2$); 25.7 (CH$_2$); 29.5 (—NCH$_3$); 29.6 (CH$_2$); 32.0 (CH$_2$); 35.7 (CH$_2$); 43.4 (CH—P); 46.1 (CH$_2$); 49.8 (CH$_2$); 55.8 (CH$_2$); 65.9 (CH—B); 73.1; 81.0; 104.3; 123.0; 124.6 (CH); 126.4 (CH); 129.8 (CH); 133.0 (CH); 148.0; 149.8; 151.8; 154.3; 156.1; 161.1; 168.2; 169.3 (CH=N)

The compounds of formula (V) obtained according to the examples 24 to 27 have been converted to Linagliptin following the procedure reported in Example 9, obtaining comparable results.

The invention claimed is:
1. A compound of formula (V):

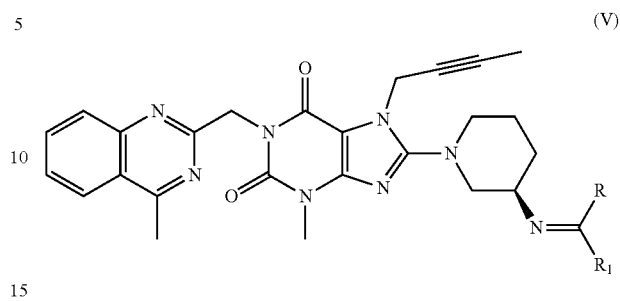

wherein one of R and $R_1$ is H and the other of R and $R_1$ is selected from the group consisting of optionally substituted C5-C6 cycloalkyl, optionally substituted C3-C9 alkenyl, optionally substituted phenyl and optionally substituted straight or branched C1-C6 alkyl.

2. The compound according to claim 1 wherein said other of R and $R_1$ is selected from the group consisting of methyl, ethyl, propyl, isopropyl, butyl, isobutyl, sec-butyl, tert-butyl, phenyl, benzyl, p-tolyl, p-methoxyphenyl, m-methoxyphenyl, p-nitrophenyl, p-chlorophenyl, 3,4-dimethoxyphenyl, cyclopentyl and cyclohexyl.

3. The compound according to claim 2 wherein R is hydrogen and $R_1$ is phenyl.

4. Process for the preparation of Linagliptin, which comprises:
(a) the reaction of a compound of formula (II) with a compound of formula (VI) to give compounds of formula (V)

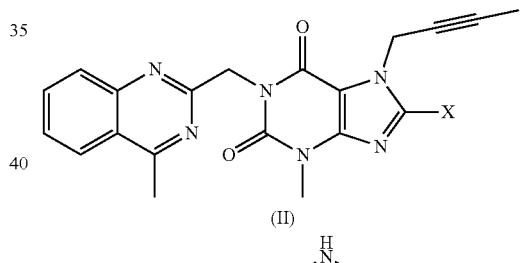

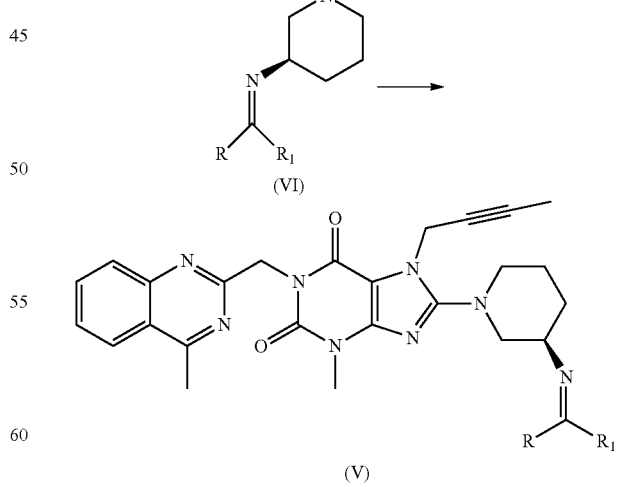

wherein X is a halogen selected from Cl and Br
and R and $R_1$ have the meanings reported in claim 1,
in presence of a base in a suitable solvent and optionally of a phase transfer agent, (b) the deprotection of intermediates of formula (V), optionally isolated, to give Linagliptin and the optional subsequent formation of a salt thereof.

5. The process according to claim 4 wherein in step (a) the base is selected from alkali and alkaline-earth metal hydroxides, carbonates, bicarbonates and phosphates, or mixtures thereof; the solvent is selected from aprotic apolar or polar, aromatic, aliphatic, ether, ester, keto solvents or mixtures thereof having a water content ranging from 0% to 6% (v/v); the optional phase transfer agent is selected from tetrasubstituted ammonium or phosphonium salts and the molar ratio of compound of formula (II) to compound of formula (VI) ranges from 1/1 to 1/1.5; optional isolation in step (b) is effected by precipitation or crystallization in the presence of a straight or branched C1-C4 alcohol or of an ester or ether or mixtures thereof in the presence of aprotic apolar or polar, aromatic, aliphatic solvents or mixtures thereof and the deprotection is effected under mildly acid or basic conditions.

6. The process according to claim 5 wherein in step (a) the base is selected from sodium carbonate, potassium carbonate, cesium carbonate, sodium phosphate, potassium phosphate; solvents are selected from acetonitrile, dimethylsulfoxide, sulfolane, N-methylpyrrolidone, dimethylformamide, toluene, xylenes, cumene, cymene, valerolactone, cyclopentyl methyl ether, methyl isobutyl ketone or mixtures thereof; the isolation in step (b) is effected in methanol or ethyl acetate or isopropyl acetate or mixtures thereof in the presence of acetonitrile, dimethylsulfoxide, sulfolane, N-methylpyrrolidone, dimethylformamide, toluene, xylenes, cumene, cymene, valerolactone, cyclopentyl methyl ether, methyl isobutyl ketone or mixtures thereof optionally in the presence of methyl-t-butyl ether and the deprotection is effected using an organic aqueous diphasic system in the presence of an acid or, alternatively, an organic system with a base, at a temperature ranging from 0° C. to 30° C.

7. The process according to claim 6 wherein in step (a) the base is potassium carbonate or potassium phosphate, the solvent is toluene containing a water percentage ranging from 0% to 6% (v/v) and a N-methylpyrrolidone percentage between 0% and 10% (v/v); in step (b) isolation is effected by precipitation or crystallization in the presence of toluene and methanol in admixture with methyl-t-butyl ether and the deprotection if using an organic aqueous diphasic system in the presence of an acid, said acid is selected from straight, branched or cyclic C1-C8, in the presence of aromatic, aliphatic, ether, chlorinated solvents or mixtures thereof; if using an organic system with a base, said base is selected from T-NH$_2$ amines wherein T is straight or branched C1-C8 alkyl, or an OZ group wherein Z is H or C1-C6 alkyl; or mixtures thereof in the presence of aromatic, aliphatic, alcoholic, ether, chlorinate solvent or mixtures thereof.

8. The process according to claim 7 wherein in step (b) if using an organic aqueous diphasic system in the presence of an acid, said acid is acetic acid in the presence of toluene; if using an organic system with a base, said base is selected from methylamine, ethylamine, triethylamine, n-butylamine, t-butylamine, methoxylamine, ethoxylamine, hydroxylamine or salts thereof or mixtures thereof in the presence of methylene chloride, methyltetrahydrofuran, cyclopentyl methyl ether, acetonitrile, ethanol, methanol, isopropanol, n-propanol, n-butanol, t-butanol, sec-butanol, toluene, xylenes, cumene, cymene or mixtures thereof.

9. The process according to claim 8 wherein in step (b) if using an organic system with a base, said base is hydroxylamine or salts thereof in the presence of toluene or ethanol or mixtures thereof.

10. The process according to claim 4, further comprising the preparation of a pharmaceutical composition of Linagliptin or a pharmacologically acceptable salt thereof in mixture with one or more conventional pharmaceutical additives.

11. The process according to claim 5, further comprising the preparation of a pharmaceutical composition of Linagliptin or a pharmacologically acceptable salt thereof in mixture with one or more conventional pharmaceutical additives.

12. The process according to claim 6, further comprising the preparation of a pharmaceutical composition of Linagliptin or a pharmacologically acceptable salt thereof in mixture with one or more conventional pharmaceutical additives.

13. The process according to claim 7, further comprising the preparation of a pharmaceutical composition of Linagliptin or a pharmacologically acceptable salt thereof in mixture with one or more conventional pharmaceutical additives.

14. The process according to claim 8, further comprising the preparation of a pharmaceutical composition of Linagliptin or a pharmacologically acceptable salt thereof in mixture with one or more conventional pharmaceutical additives.

15. The process according to claim 9, further comprising the preparation of a pharmaceutical composition of Linagliptin or a pharmacologically acceptable salt thereof in mixture with one or more conventional pharmaceutical additives.

* * * * *